United States Patent [19]
Holly et al.

[11] Patent Number: 5,476,777
[45] Date of Patent: Dec. 19, 1995

[54] METHODS FOR PRODUCING THROMBIN

[75] Inventors: Richard D. Holly; Donald C. Foster, both of Seattle, Wash.

[73] Assignee: Zymogenetics, Inc., Seattle, Wash.

[21] Appl. No.: 998,972

[22] Filed: Dec. 30, 1992

Related U.S. Application Data

[63] Continuation-in-part of Ser. No. 860,701, Mar. 31, 1992, abandoned, which is a continuation-in-part of Ser. No. 816,281, Dec. 31, 1991, abandoned.

[51] Int. Cl.$^6$ .............................. C12N 9/74; C12N 1/20; C12N 1/14; C12P 21/06
[52] U.S. Cl. ........................ 435/214; 435/69.1; 435/69.6; 435/240.2; 435/320.1; 435/254.11; 435/254.2; 435/254.21; 424/94.64; 530/350; 530/380; 530/381; 530/382; 536/22.1; 536/23.1; 536/23.2; 536/23.5
[58] Field of Search ...................... 424/96.64; 435/69.1, 435/69.6, 214, 240.2, 320.1, 254.11, 254.2, 254.21; 530/350, 380, 381, 382; 536/22.1, 23.1, 23.2, 23.5

[56] References Cited

FOREIGN PATENT DOCUMENTS

| | | |
|---|---|---|
| 443724 | 8/1991 | European Pat. Off. . |
| 9005533 | 7/1990 | Rep. of Korea . |
| 9111519 | 8/1991 | WIPO . |

OTHER PUBLICATIONS

Heldebrant et al., "The Activation of Prothrombin", *J. Biol. Chem.* 248: 7149–7163, (Oct. 25, 1973).
Downing et al., "Human Prothrombin Activation", *J. Biol. Chem.* 250: 8897–8906, (Dec. 10, 1975).
Jackson and Nemerson, "Blood Coagulation", *Ann. Rev. Biochem.* 49: 765–811, (1980).
Malhotra et al., "The Kinetics of Activation of Normal and λ–Carboxyglutamic Acid–deficient Prothrombins" *J. Biol. Chem.* 260: 279–287, (Jan. 10, 1983).
Blanchard et al., "Immunoassays of Human Prothrombin Species which correlate with Funcitonal Coagulant Activities", *J. Lab. Clin. Med.* 101: 242–255, (Feb., 1983).
Degen et al., "Characterization of the Complementary Deoxyribonucleic Acid Gene Coding for Human Prothrombin", *Biochemistry* 22: 2087–2097, (1983).
Glover, "Expression of Cloned Genes in Animal Cells", *Gene Cloning*, Ed. Brammar, Chapman and Hall, N.Y. pp. 179–219 (1984).
Foster et al., "Propeptide of Human Protein C is Necessary for λ–Carboxylation", *Biochemistry* 26: 7003–7011, (1987).
Degen and Davie, "Nucleotide Sequence of the Gene for Human Prothrombin", *Biochemistry* 26: 6165–6177, (1987).
Krishnaswamy et al., "Activation of Human Prothrombin by Human Prothrombinase", *J. Biol. Chem.* 262:3291–3299 (1987).
Rosing et al., "Calcium–Independent Activation of Prothromnin on Membranes with Positively Charged Lipids" *Biochem.* 27:9048–9055 (1988).
Teng et al. "Effects of Venom Proteases on Peptide Chromogenic Substrates and Bovine Prothrombin", *Taxicon.* 27: 161–167, (1989).

*Primary Examiner*—Charles L. Patterson, Jr.
*Assistant Examiner*—Hyosuk Kim
*Attorney, Agent, or Firm*—Townsend and Townsend and Crew

[57] ABSTRACT

Methods are disclosed for producing thrombin. The protein is produced from host cells transformed or transfected with DNA construct(s) containing information necessary to direct the expression of thrombin precursors. The DNA constructs generally include the following operably linked elements: a transcriptional promoter, DNA sequence encoding a gla-domainless prothrombin, and a transcriptional terminator. Thrombin precursors produced from transformed or transfected host cells are activated either in vivo or in vitro.

31 Claims, 2 Drawing Sheets

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CCNGCRCARA ACAT                                                          14

( 2 ) INFORMATION FOR SEQ ID NO:2:

( i ) SEQUENCE CHARACTERISTICS:
        ( A ) LENGTH: 1947 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: Homo sapiens
        ( F ) TISSUE TYPE: Hepatic ( i x ) FEATURE:
        ( A ) NAME/KEY: CDS
        ( B ) LOCATION: 3..1847

( x i ) SEQUENCE DESCRIPTION: SEQ ID NO:2:

```
TG CAG CTG CCT GGC TGC CTG GCC CTG GCT GCC CTG TGT AGC CTT GTG        47
   Gln Leu Pro Gly Cys Leu Ala Leu Ala Ala Leu Cys Ser Leu Val
    1               5                  10                  15

CAC AGC CAG CAT GTG TTC CTG GCT CCT CAG CAA GCA CGG TCG CTG CTC        95
His Ser Gln His Val Phe Leu Ala Pro Gln Gln Ala Arg Ser Leu Leu
                20                  25                  30

CAG CGG GTC CGG CGA GCC AAC ACC TTC TTG GAG GAG GTG CGC AAG GGC       143
Gln Arg Val Arg Arg Ala Asn Thr Phe Leu Glu Glu Val Arg Lys Gly
            35                  40                  45

AAC CTA GAG CGA GAG TGC GTG GAG GAG ACG TGC AGC TAC GAG GAG GCC       191
Asn Leu Glu Arg Glu Cys Val Glu Glu Thr Cys Ser Tyr Glu Glu Ala
        50                  55                  60

TTC GAG GCT CTG GAG TCC TCC ACG GCT ACG GAT GTG TTC TGG GCC AAG       239
Phe Glu Ala Leu Glu Ser Ser Thr Ala Thr Asp Val Phe Trp Ala Lys
    65                  70                  75

TAC ACA GCT TGT GAG ACA GCG AGG ACG CCT CGA GAT AAG CTT GCT GCA       287
Tyr Thr Ala Cys Glu Thr Ala Arg Thr Pro Arg Asp Lys Leu Ala Ala
80                  85                  90                  95

TGT CTG GAA GGT AAC TGT GCT GAG GGT CTG GGT ACG AAC TAC CGA GGG       335
Cys Leu Glu Gly Asn Cys Ala Glu Gly Leu Gly Thr Asn Tyr Arg Gly
                100                 105                 110

CAT GTG AAC ATC ACC CGG TCA GGC ATT GAG TGC CAG CTA TGG AGG AGT       383
His Val Asn Ile Thr Arg Ser Gly Ile Glu Cys Gln Leu Trp Arg Ser
            115                 120                 125

CGC TAC CCA CAT AAG CCT GAA ATC AAC TCC ACT ACC CAT CCT GGG GCC       431
Arg Tyr Pro His Lys Pro Glu Ile Asn Ser Thr Thr His Pro Gly Ala
        130                 135                 140

GAC CTA CAG GAG AAT TTC TGC CGC AAC CCC GAC AGC AGC AAC ACG GGA       479
Asp Leu Gln Glu Asn Phe Cys Arg Asn Pro Asp Ser Ser Asn Thr Gly
    145                 150                 155
```

| | | | | | | | | | | | | | | | | |
|---|---|---|---|---|---|---|---|---|---|---|---|---|---|---|---|---|
| CCC | TGG | TGC | TAC | ACT | ACA | GAC | CCC | ACC | GTG | AGG | AGG | CAG | GAA | TGC | AGC | 527 |
| Pro | Trp | Cys | Tyr | Thr | Thr | Asp | Pro | Thr | Val | Arg | Arg | Gln | Glu | Cys | Ser | |
| 160 | | | | | 165 | | | | | 170 | | | | | 175 | |
| ATC | CCT | GTC | TGT | GGC | CAG | GAT | CAA | GTC | ACT | GTA | GCG | ATG | ACT | CCA | CGC | 575 |
| Ile | Pro | Val | Cys | Gly | Gln | Asp | Gln | Val | Thr | Val | Ala | Met | Thr | Pro | Arg | |
| | | | | 180 | | | | | 185 | | | | | 190 | | |
| TCC | GAA | GGC | TCC | AGT | GTG | AAT | CTG | TCA | CCT | CCA | TTG | GAG | CAG | TGT | GTC | 623 |
| Ser | Glu | Gly | Ser | Ser | Val | Asn | Leu | Ser | Pro | Pro | Leu | Glu | Gln | Cys | Val | |
| | | | 195 | | | | | 200 | | | | | 205 | | | |
| CCT | GAT | CGG | GGG | CAG | CAG | TAC | CAG | GGG | CGC | CTG | GCG | GTG | ACC | ACA | CAT | 671 |
| Pro | Asp | Arg | Gly | Gln | Gln | Tyr | Gln | Gly | Arg | Leu | Ala | Val | Thr | Thr | His | |
| 210 | | | | | 215 | | | | | 220 | | | | | | |
| GGG | CTC | CCC | TGC | CTG | GCC | TGG | GCC | AGC | GCA | CAG | GCC | AAG | GCC | CTG | AGC | 719 |
| Gly | Leu | Pro | Cys | Leu | Ala | Trp | Ala | Ser | Ala | Gln | Ala | Lys | Ala | Leu | Ser | |
| | 225 | | | | | 230 | | | | | 235 | | | | | |
| AAG | CAC | CAG | GAC | TTC | AAC | TCA | GCT | GTG | CAG | CTG | GTG | GAG | AAC | TTC | TGC | 767 |
| Lys | His | Gln | Asp | Phe | Asn | Ser | Ala | Val | Gln | Leu | Val | Glu | Asn | Phe | Cys | |
| 240 | | | | | 245 | | | | | 250 | | | | | 255 | |
| CGC | AAC | CCA | GAC | GGG | GAT | GAG | GAG | GGC | GTG | TGG | TGC | TAT | GTG | GCC | GGG | 815 |
| Arg | Asn | Pro | Asp | Gly | Asp | Glu | Glu | Gly | Val | Trp | Cys | Tyr | Val | Ala | Gly | |
| | | | | 260 | | | | | 265 | | | | | 270 | | |
| AAG | CCT | GGC | GAC | TTT | GGG | TAC | TGC | GAC | CTC | AAC | TAT | TGT | GAG | GAG | GCC | 863 |
| Lys | Pro | Gly | Asp | Phe | Gly | Tyr | Cys | Asp | Leu | Asn | Tyr | Cys | Glu | Glu | Ala | |
| | | | 275 | | | | | 280 | | | | | 285 | | | |
| GTG | GAG | GAG | GAG | ACA | GGA | GAT | GGG | CTG | GAT | GAG | GAC | TCA | GAC | AGG | GCC | 911 |
| Val | Glu | Glu | Glu | Thr | Gly | Asp | Gly | Leu | Asp | Glu | Asp | Ser | Asp | Arg | Ala | |
| | | 290 | | | | | 295 | | | | | 300 | | | | |
| ATC | GAA | GGG | CGT | ACC | GCC | ACA | AGT | GAG | TAC | CAG | ACT | TTC | TTC | AAT | CCG | 959 |
| Ile | Glu | Gly | Arg | Thr | Ala | Thr | Ser | Glu | Tyr | Gln | Thr | Phe | Phe | Asn | Pro | |
| 305 | | | | | 310 | | | | | 315 | | | | | | |
| AGG | ACC | TTT | GGC | TCG | GGA | GAG | GCA | GAC | TGT | GGG | CTG | CGA | CCT | CTG | TTC | 1007 |
| Arg | Thr | Phe | Gly | Ser | Gly | Glu | Ala | Asp | Cys | Gly | Leu | Arg | Pro | Leu | Phe | |
| 320 | | | | 325 | | | | | 330 | | | | | 335 | | |
| GAG | AAG | AAG | TCG | CTG | GAG | GAC | AAA | ACC | GAA | AGA | GAG | CTC | CTG | GAA | TCC | 1055 |
| Glu | Lys | Lys | Ser | Leu | Glu | Asp | Lys | Thr | Glu | Arg | Glu | Leu | Leu | Glu | Ser | |
| | | | | 340 | | | | | 345 | | | | | 350 | | |
| TAC | ATC | GAC | GGG | CGC | ATT | GTG | GAG | GGC | TCG | GAT | GCA | GAG | ATC | GGC | ATG | 1103 |
| Tyr | Ile | Asp | Gly | Arg | Ile | Val | Glu | Gly | Ser | Asp | Ala | Glu | Ile | Gly | Met | |
| | | | 355 | | | | | 360 | | | | | 365 | | | |
| TCA | CCT | TGG | CAG | GTG | ATG | CTT | TTC | CGG | AAG | AGT | CCC | CAG | GAG | CTG | CTG | 1151 |
| Ser | Pro | Trp | Gln | Val | Met | Leu | Phe | Arg | Lys | Ser | Pro | Gln | Glu | Leu | Leu | |
| | | 370 | | | | | 375 | | | | | 380 | | | | |
| TGT | GGG | GCC | AGC | CTC | ATC | AGT | GAC | CGC | TGG | GTC | CTC | ACC | GCC | GCC | CAC | 1199 |
| Cys | Gly | Ala | Ser | Leu | Ile | Ser | Asp | Arg | Trp | Val | Leu | Thr | Ala | Ala | His | |
| | 385 | | | | | 390 | | | | | 395 | | | | | |
| TGC | CTC | CTG | TAC | CCG | CCC | TGG | GAC | AAG | AAC | TTC | ACC | GAG | AAT | GAC | CTT | 1247 |
| Cys | Leu | Leu | Tyr | Pro | Pro | Trp | Asp | Lys | Asn | Phe | Thr | Glu | Asn | Asp | Leu | |
| 400 | | | | | 405 | | | | | 410 | | | | | 415 | |
| CTG | GTG | CGC | ATT | GGC | AAG | CAC | TCC | CGC | ACC | AGG | TAC | GAG | CGA | AAC | ATT | 1295 |
| Leu | Val | Arg | Ile | Gly | Lys | His | Ser | Arg | Thr | Arg | Tyr | Glu | Arg | Asn | Ile | |
| | | | | 420 | | | | | 425 | | | | | 430 | | |
| GAA | AAG | ATA | TCC | ATG | TTG | GAA | AAG | ATC | TAC | ATC | CAC | CCC | AGG | TAC | AAC | 1343 |
| Glu | Lys | Ile | Ser | Met | Leu | Glu | Lys | Ile | Tyr | Ile | His | Pro | Arg | Tyr | Asn | |
| | | | 435 | | | | | 440 | | | | | 445 | | | |
| TGG | CGG | GAG | AAC | CTG | GAC | CGG | GAC | ATT | GCC | CTG | ATG | AAG | CTG | AAG | AAG | 1391 |
| Trp | Arg | Glu | Asn | Leu | Asp | Arg | Asp | Ile | Ala | Leu | Met | Lys | Leu | Lys | Lys | |
| | | 450 | | | | | 455 | | | | | 460 | | | | |
| CCT | GTT | GCC | TTC | AGT | GAC | TAC | ATT | CAC | CCT | GTG | TGT | CTG | CCC | GAC | AGG | 1439 |
| Pro | Val | Ala | Phe | Ser | Asp | Tyr | Ile | His | Pro | Val | Cys | Leu | Pro | Asp | Arg | |
| | 465 | | | | | 470 | | | | | 475 | | | | | |

```
GAG  ACG  GCA  GCC  AGC  TTG  CTC  CAG  GCT  GGA  TAC  AAG  GGG  CGG  GTG  ACA       1487
Glu  Thr  Ala  Ala  Ser  Leu  Leu  Gln  Ala  Gly  Tyr  Lys  Gly  Arg  Val  Thr
480                      485                      490                      495

GGC  TGG  GGC  AAC  CTG  AAG  GAG  ACG  TGG  ACA  GCC  AAC  GTT  GGT  AAG  GGG       1535
Gly  Trp  Gly  Asn  Leu  Lys  Glu  Thr  Trp  Thr  Ala  Asn  Val  Gly  Lys  Gly
                         500                      505                      510

CAG  CCC  AGT  GTC  CTG  CAG  GTG  GTG  AAC  CTG  CCC  ATT  GTG  GAG  CGG  CCG       1583
Gln  Pro  Ser  Val  Leu  Gln  Val  Val  Asn  Leu  Pro  Ile  Val  Glu  Arg  Pro
               515                      520                      525

GTC  TGC  AAG  GAC  TCC  ACC  CGG  ATC  CGC  ATC  ACT  GAC  AAC  ATG  TTC  TGT       1631
Val  Cys  Lys  Asp  Ser  Thr  Arg  Ile  Arg  Ile  Thr  Asp  Asn  Met  Phe  Cys
          530                      535                      540

GCT  GGT  TAC  AAG  CCT  GAT  GAA  GGG  AAA  CGA  GGG  GAT  GCC  TGT  GAA  GGT       1679
Ala  Gly  Tyr  Lys  Pro  Asp  Glu  Gly  Lys  Arg  Gly  Asp  Ala  Cys  Glu  Gly
545                      550                      555

GAC  AGT  GGG  GGA  CCC  TTT  GTC  ATG  AAG  AGC  CCC  TTT  AAC  AAC  CGC  TGG       1727
Asp  Ser  Gly  Gly  Pro  Phe  Val  Met  Lys  Ser  Pro  Phe  Asn  Asn  Arg  Trp
560                      565                      570                      575

TAT  CAA  ATG  GGC  ATC  GTC  TCA  TGG  GGT  GAA  GGC  TGT  GAC  CGG  GAT  GGG       1775
Tyr  Gln  Met  Gly  Ile  Val  Ser  Trp  Gly  Glu  Gly  Cys  Asp  Arg  Asp  Gly
               580                      585                      590

AAA  TAT  GGC  TTC  TAC  ACA  CAT  GTG  TTC  CGC  CTG  AAG  AAG  TGG  ATA  CAG       1823
Lys  Tyr  Gly  Phe  Tyr  Thr  His  Val  Phe  Arg  Leu  Lys  Lys  Trp  Ile  Gln
          595                      600                      605

AAG  GTC  ATT  GAT  CAG  TTT  GGA  GAG  TAGGGGCCA  CTCATATTCT  GGGCTCCTGG            1877
Lys  Val  Ile  Asp  Gln  Phe  Gly  Glu
               610                      615

AACCAATCCC  GTGAAAGAAT  TATTTTTGTG  TTTCTAAAAC  TATGGTTCCC  AATAAAAGTG               1937

ACTCTCAGCG                                                                            1947
```

( 2 ) INFORMATION FOR SEQ ID NO:3:

( i ) SEQUENCE CHARACTERISTICS:
        ( A ) LENGTH: 615 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Gln  Leu  Pro  Gly  Cys  Leu  Ala  Leu  Ala  Ala  Leu  Cys  Ser  Leu  Val  His
1                 5                       10                      15

Ser  Gln  His  Val  Phe  Leu  Ala  Pro  Gln  Gln  Ala  Arg  Ser  Leu  Leu  Gln
               20                      25                      30

Arg  Val  Arg  Arg  Ala  Asn  Thr  Phe  Leu  Glu  Glu  Val  Arg  Lys  Gly  Asn
          35                      40                      45

Leu  Glu  Arg  Glu  Cys  Val  Glu  Glu  Thr  Cys  Ser  Tyr  Glu  Glu  Ala  Phe
     50                      55                      60

Glu  Ala  Leu  Glu  Ser  Ser  Thr  Ala  Thr  Asp  Val  Phe  Trp  Ala  Lys  Tyr
65                       70                      75                      80

Thr  Ala  Cys  Glu  Thr  Ala  Arg  Thr  Pro  Arg  Asp  Lys  Leu  Ala  Ala  Cys
               85                      90                      95

Leu  Glu  Gly  Asn  Cys  Ala  Glu  Gly  Leu  Gly  Thr  Asn  Tyr  Arg  Gly  His
          100                     105                     110

Val  Asn  Ile  Thr  Arg  Ser  Gly  Ile  Glu  Cys  Gln  Leu  Trp  Arg  Ser  Arg
     115                     120                     125

Tyr  Pro  His  Lys  Pro  Glu  Ile  Asn  Ser  Thr  Thr  His  Pro  Gly  Ala  Asp
130                     135                     140
```

```
Leu Gln Glu Asn Phe Cys Arg Asn Pro Asp Ser Ser Asn Thr Gly Pro
145                 150                 155                 160

Trp Cys Tyr Thr Thr Asp Pro Thr Val Arg Arg Gln Glu Cys Ser Ile
            165                 170                 175

Pro Val Cys Gly Gln Asp Gln Val Thr Val Ala Met Thr Pro Arg Ser
            180                 185                 190

Glu Gly Ser Ser Val Asn Leu Ser Pro Pro Leu Glu Gln Cys Val Pro
            195                 200                 205

Asp Arg Gly Gln Gln Tyr Gln Gly Arg Leu Ala Val Thr Thr His Gly
        210             215                 220

Leu Pro Cys Leu Ala Trp Ala Ser Ala Gln Ala Lys Ala Leu Ser Lys
225             230                 235                 240

His Gln Asp Phe Asn Ser Ala Val Gln Leu Val Glu Asn Phe Cys Arg
                245                 250                 255

Asn Pro Asp Gly Asp Glu Glu Gly Val Trp Cys Tyr Val Ala Gly Lys
            260                 265                 270

Pro Gly Asp Phe Gly Tyr Cys Asp Leu Asn Tyr Cys Glu Glu Ala Val
        275                 280                 285

Glu Glu Glu Thr Gly Asp Gly Leu Asp Glu Asp Ser Asp Arg Ala Ile
290                 295                 300

Glu Gly Arg Thr Ala Thr Ser Glu Tyr Gln Thr Phe Phe Asn Pro Arg
305                 310                 315                 320

Thr Phe Gly Ser Gly Glu Ala Asp Cys Gly Leu Arg Pro Leu Phe Glu
            325                 330                 335

Lys Lys Ser Leu Glu Asp Lys Thr Glu Arg Glu Leu Leu Glu Ser Tyr
            340                 345                 350

Ile Asp Gly Arg Ile Val Glu Gly Ser Asp Ala Glu Ile Gly Met Ser
        355                 360                 365

Pro Trp Gln Val Met Leu Phe Arg Lys Ser Pro Gln Glu Leu Leu Cys
        370                 375                 380

Gly Ala Ser Leu Ile Ser Asp Arg Trp Val Leu Thr Ala Ala His Cys
385                 390                 395                 400

Leu Leu Tyr Pro Pro Trp Asp Lys Asn Phe Thr Glu Asn Asp Leu Leu
            405                 410                 415

Val Arg Ile Gly Lys His Ser Arg Thr Arg Tyr Glu Arg Asn Ile Glu
            420                 425                 430

Lys Ile Ser Met Leu Glu Lys Ile Tyr Ile His Pro Arg Tyr Asn Trp
        435                 440                 445

Arg Glu Asn Leu Asp Arg Asp Ile Ala Leu Met Lys Leu Lys Lys Pro
450                 455                 460

Val Ala Phe Ser Asp Tyr Ile His Pro Val Cys Leu Pro Asp Arg Glu
465                 470                 475                 480

Thr Ala Ala Ser Leu Leu Gln Ala Gly Tyr Lys Gly Arg Val Thr Gly
            485                 490                 495

Trp Gly Asn Leu Lys Glu Thr Trp Thr Ala Asn Val Gly Lys Gly Gln
            500                 505                 510

Pro Ser Val Leu Gln Val Val Asn Leu Pro Ile Val Glu Arg Pro Val
        515                 520                 525

Cys Lys Asp Ser Thr Arg Ile Arg Ile Thr Asp Asn Met Phe Cys Ala
        530                 535                 540

Gly Tyr Lys Pro Asp Glu Gly Lys Arg Gly Asp Ala Cys Glu Gly Asp
545                 550                 555                 560
```

```
Ser  Gly  Gly  Pro  Phe  Val  Met  Lys  Ser  Pro  Phe  Asn  Asn  Arg  Trp  Tyr
               565                       570                      575

Gln  Met  Gly  Ile  Val  Ser  Trp  Gly  Glu  Gly  Cys  Asp  Arg  Asp  Gly  Lys
               580                       585                      590

Tyr  Gly  Phe  Tyr  Thr  His  Val  Phe  Arg  Leu  Lys  Lys  Trp  Ile  Gln  Lys
          595                      600                      605

Val  Ile  Asp  Gln  Phe  Gly  Glu
     610                      615
```

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC1237

( x i ) SEQUENCE DESCRIPTION: SEQ ID NO:4:

```
GATCTGCCAA CTCCTTCCTG GAGGAGCT                                           28
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC1238

( x i ) SEQUENCE DESCRIPTION: SEQ ID NO:5:

```
CCTCCAGGAA GGAGTTGGCA                                                    20
```

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC1323

( x i ) SEQUENCE DESCRIPTION: SEQ ID NO:6:

```
CCTCCAGGAA GGAGTTGGCT CGCCGGA                                            27
```

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC1324

( x i ) SEQUENCE DESCRIPTION: SEQ ID NO:7:

```
CGCGTCCGGC GAGCCAACTC CTTCCTGGAG GAGCT                                   35
```

( 2 ) INFORMATION FOR SEQ ID NO:8:

( i ) SEQUENCE CHARACTERISTICS:
  ( A ) LENGTH: 126 base pairs
  ( B ) TYPE: nucleic acid
  ( C ) STRANDEDNESS: single
  ( D ) TOPOLOGY: linear ( v i i ) IMMEDIATE SOURCE:
  ( B ) CLONE: ZC1378

( x i ) SEQUENCE DESCRIPTION: SEQ ID NO:8:

```
AATTCCACCA TGGCTCATGT GAGAGGACTG CAACTGCCTG GCTGCCTGGC TCTGGCTGCT         60
CTGTGCAGCC TGGTGCACAG CCAGCATGTG TTCCTGGCTC CTCAGCAGGC CAGGAGCCTG        120
CTGCAA                                                                   126
```

( 2 ) INFORMATION FOR SEQ ID NO:9:

( i ) SEQUENCE CHARACTERISTICS:
  ( A ) LENGTH: 126 base pairs
  ( B ) TYPE: nucleic acid
  ( C ) STRANDEDNESS: single
  ( D ) TOPOLOGY: linear ( v i i ) IMMEDIATE SOURCE:
  ( B ) CLONE: ZC1379

( x i ) SEQUENCE DESCRIPTION: SEQ ID NO:9:

```
CGCGTTGCAG CAGGCTCCTG GCCTGCTGAG GAGCCAGGAA CACATGCTGG CTGTGCACCA         60
GGCTGCACAG AGCAGCCAGA GCCAGGCAGC CAGGCAGTTG CAGTCCTCTC ACATGAGCCA        120
TGGTGG                                                                   126
```

( 2 ) INFORMATION FOR SEQ ID NO:10:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( v i i ) IMMEDIATE SOURCE:
  ( B ) CLONE: ZC2490

( x i ) SEQUENCE DESCRIPTION: SEQ ID NO:10:

```
AATTCTACAC AATGCTGCA                                                      19
```

( 2 ) INFORMATION FOR SEQ ID NO:11:

( i ) SEQUENCE CHARACTERISTICS:
  ( A ) LENGTH: 11 base pairs
  ( B ) TYPE: nucleic acid
  ( C ) STRANDEDNESS: single
  ( D ) TOPOLOGY: linear ( v i i ) IMMEDIATE SOURCE:
  ( B ) CLONE: ZC2492

( x i ) SEQUENCE DESCRIPTION: SEQ ID NO:11:

```
GCATTGTGTA G                                                              11
```

( 2 ) INFORMATION FOR SEQ ID NO:12:

( i ) SEQUENCE CHARACTERISTICS:
  ( A ) LENGTH: 56 base pairs
  ( B ) TYPE: nucleic acid
  ( C ) STRANDEDNESS: single
  ( D ) TOPOLOGY: linear ( v i i ) IMMEDIATE SOURCE:

(B) CLONE: ZC3830

(xi) SEQUENCE DESCRIPTION: SEQ ID NO:12:

GCGCGCTCCT CTTCTGAATC GGGCATGGAT TTCCTGGCTG GGCGAAACGA AGACGG    56

(2) INFORMATION FOR SEQ ID NO:13:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (vii) IMMEDIATE SOURCE:
        (B) CLONE: ZC3831

(xi) SEQUENCE DESCRIPTION: SEQ ID NO:13:

GCGCGCACCG CCACAAGTGA GTACCAGACT TTCTTCAATC CGAGGACCTT TGGC    54

(2) INFORMATION FOR SEQ ID NO:14:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (vii) IMMEDIATE SOURCE:
        (B) CLONE: ZC3832

(xi) SEQUENCE DESCRIPTION: SEQ ID NO:14:

CCGAGCCAAA GGTCCTAGGA TTGAAGAAAG TCTGGTACTC ACTTGTGGCG GT    52

(2) INFORMATION FOR SEQ ID NO:15:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (vii) IMMEDIATE SOURCE:
        (B) CLONE: ZC3833

(xi) SEQUENCE DESCRIPTION: SEQ ID NO:15:

CGCCGTCTTC GTTTCGCCCA GCCAGGAAAT CCATGCCCGA TTCAGAAGAG GA    52

(2) INFORMATION FOR SEQ ID NO:16:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (vii) IMMEDIATE SOURCE:
        (B) CLONE: ZC3858

(xi) SEQUENCE DESCRIPTION: SEQ ID NO:16:

GATCTGAAGG CTCCAGTGTG AATCTGTCAC CTCCACTCGA GCAGTGTGTC CCTGATCGGG    60

GGCAGCAGTA CCAGGGGCGC    80

(2) INFORMATION FOR SEQ ID NO:17:

(i) SEQUENCE CHARACTERISTICS:
        (A) LENGTH: 72 base pairs
        (B) TYPE: nucleic acid
        (C) STRANDEDNESS: single (D) TOPOLOGY: linear (vii) IMMEDIATE SOURCE:
    (B) CLONE: ZC3859

(xi) SEQUENCE DESCRIPTION: SEQ ID NO:17:

```
CCCTGGTACT GCTGCCCCCG ATCAGGGACA CACTGCTCGA GTGGAGGTGA CAGATTCACA        60
CTGGAGCCTT CA                                                            72
```

(2) INFORMATION FOR SEQ ID NO:18:

(i) SEQUENCE CHARACTERISTICS:
       (A) LENGTH: 64 base pairs
       (B) TYPE: nucleic acid
       (C) STRANDEDNESS: single
       (D) TOPOLOGY: linear (vii) IMMEDIATE SOURCE:
       (B) CLONE: ZC3860

(xi) SEQUENCE DESCRIPTION: SEQ ID NO:18:

```
GATCTTCCAC GGCTACGGAT GTGTTCTGGG CCAAGTACAC AGCTTGTGAG ACAGCGCGCA        60
CGCC                                                                    64
```

(2) INFORMATION FOR SEQ ID NO:19:

(i) SEQUENCE CHARACTERISTICS:
       (A) LENGTH: 64 base pairs
       (B) TYPE: nucleic acid
       (C) STRANDEDNESS: single
       (D) TOPOLOGY: linear (vii) IMMEDIATE SOURCE:
       (B) CLONE: ZC3861

(xi) SEQUENCE DESCRIPTION: SEQ ID NO:19:

```
TCGAGGCGTG CGCGCTGTCT CACAAGCTGT GTACTTGGCC CAGAACACAT CCGTAGCCGT        60
GGAA                                                                    64
```

(2) INFORMATION FOR SEQ ID NO:20:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (vii) IMMEDIATE SOURCE:
       (B) CLONE: ZC4393

(xi) SEQUENCE DESCRIPTION: SEQ ID NO:20:

```
CTCTCCCGAG CCAAAGGTCT GCGGATT                                            27
```

(2) INFORMATION FOR SEQ ID NO:21:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (vii) IMMEDIATE SOURCE:
       (B) CLONE: ZC4443

(xi) SEQUENCE DESCRIPTION: SEQ ID NO:21:

```
GTCACCGGGA ATTCATCGAT ATCTAGATCC                                         30
```

( 2 ) INFORMATION FOR SEQ ID NO:22:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC3932

( x i ) SEQUENCE DESCRIPTION: SEQ ID NO:22:

| | |
|---|---:|
| ATCCGAGCCC TCCACAATGC GCTTTCGGCG CCCGTCGATG TAGGATTCCA GGAGCT | 56 |

( 2 ) INFORMATION FOR SEQ ID NO:23:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC3933

( x i ) SEQUENCE DESCRIPTION: SEQ ID NO:23:

| | |
|---|---:|
| CCTGGAATCC TACATCGACG GGCGCCGAAA GCGCATTGTG GAGGGC | 46 |

( 2 ) INFORMATION FOR SEQ ID NO:24:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC3934

( x i ) SEQUENCE DESCRIPTION: SEQ ID NO:24:

| | |
|---|---:|
| TCGGATGCAG AGATCGGCAT GTCACCTTGG CAGGTGATGC TTTT | 44 |

( 2 ) INFORMATION FOR SEQ ID NO:25:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC3936

( x i ) SEQUENCE DESCRIPTION: SEQ ID NO:25:

| | |
|---|---:|
| CCGGAAAAGC ATCACCTGCC AAGGTGACAT GCCGATCTCT GC | 42 |

( 2 ) INFORMATION FOR SEQ ID NO:26:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4713

( x i ) SEQUENCE DESCRIPTION: SEQ ID NO:26:

| | |
|---|---:|
| CCTGGAATCC TACCGACGAA AGCGCATTGT GGAGGGA | 37 |

( 2 ) INFORMATION FOR SEQ ID NO:27:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4720

( x i ) SEQUENCE DESCRIPTION: SEQ ID NO:27:

ATCGGATCCC TCCACAATTC GCTTTCGTCG GTAGGATTCC AGGAGCT 47

( 2 ) INFORMATION FOR SEQ ID NO:28:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4721

( x i ) SEQUENCE DESCRIPTION: SEQ ID NO:28:

TCCGATGCAG AGATCGGCAT GTCACCTTGG CAGGTGATGC TTTT 44

( 2 ) INFORMATION FOR SEQ ID NO:29:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4722

( x i ) SEQUENCE DESCRIPTION: SEQ ID NO:29:

CCGGAAAAGC ATCACCTGCC AAGGTGACAT GCCGATCTCT GA 42

( 2 ) INFORMATION FOR SEQ ID NO:30:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4738

( x i ) SEQUENCE DESCRIPTION: SEQ ID NO:30:

CCTGGAATCC TACATCGACC CGCGCATTGT GGAGGGA 37

( 2 ) INFORMATION FOR SEQ ID NO:31:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4741

( x i ) SEQUENCE DESCRIPTION: SEQ ID NO:31:

TCCGATGCAG AGATCGGCAT GTCACCTTGG CAGGTGATGC TTTT 44

( 2 ) INFORMATION FOR SEQ ID NO:32:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4742

( x i ) SEQUENCE DESCRIPTION: SEQ ID NO:32:

CCGGAAAAGC ATCACCTGCC AAGGTGACAT GCCGATCTCT GC 42

( 2 ) INFORMATION FOR SEQ ID NO:33:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4781

( x i ) SEQUENCE DESCRIPTION: SEQ ID NO:33:

ATCGGATCCC TCCACAATGC GCGGGTCGAT GTAGGATTCC AGGAGCT 47

( 2 ) INFORMATION FOR SEQ ID NO:34:

( i ) SEQUENCE CHARACTERISTICS:
        ( A ) LENGTH: 4 amino acids
        ( B ) TYPE: amino acid
        ( D ) TOPOLOGY: linear ( v ) FRAGMENT TYPE: internal ( x i ) SEQUENCE DESCRIPTION: SEQ ID NO:34:

Arg Arg Lys Arg
    1

( 2 ) INFORMATION FOR SEQ ID NO:35:

( i ) SEQUENCE CHARACTERISTICS:
        ( A ) LENGTH: 4 amino acids
        ( B ) TYPE: amino acid
        ( D ) TOPOLOGY: linear ( v ) FRAGMENT TYPE: internal ( x i ) SEQUENCE DESCRIPTION: SEQ ID NO:35:

Leu Asp Lys Arg
    1

( 2 ) INFORMATION FOR SEQ ID NO:36:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: ZC1159

( x i ) SEQUENCE DESCRIPTION: SEQ ID NO:36:

```
TTGTCCAAGC TTACACCTTC                                                           20
```

( 2 ) INFORMATION FOR SEQ ID NO:37:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC1551

( x i ) SEQUENCE DESCRIPTION: SEQ ID NO:37:

```
GATCCCCGGG GAGCTCCTCG AGGCATG                                                   27
```

( 2 ) INFORMATION FOR SEQ ID NO:38:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC1552

( x i ) SEQUENCE DESCRIPTION: SEQ ID NO:38:

```
CCTCGAGGAG CTCCCCGGG                                                            19
```

( 2 ) INFORMATION FOR SEQ ID NO:39:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC1562

( x i ) SEQUENCE DESCRIPTION: SEQ ID NO:39:

```
AGCTTGGACA AGAGAACCGC TACCTCTGAA TACCAAACCT TCTTCAACCC AAGAACCTTC               60

GGTTCTGGTG                                                                      70
```

( 2 ) INFORMATION FOR SEQ ID NO:40:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC1563

( x i ) SEQUENCE DESCRIPTION: SEQ ID NO:40:

```
AAGCTGACTG TGGTTTGAGA CCATTGTTCG AAAAGAAGTC TTTGGAAGAC AAGACCGAAA               60

GAGAGCT                                                                         67
```

( 2 ) INFORMATION FOR SEQ ID NO:41:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear (v i i) IMMEDIATE SOURCE:
    (B) CLONE: ZC1564

(x i) SEQUENCE DESCRIPTION: SEQ ID NO:41:

CTCTTTCGGT CTTGTCTTCC AAAGACTTCT TTTCGAACAA TGGTCTCAAA CCACAGTCAG    60

CTTCACCAG    69

(2) INFORMATION FOR SEQ ID NO:42:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (v i i) IMMEDIATE SOURCE:
        (B) CLONE: ZC1565

(x i) SEQUENCE DESCRIPTION: SEQ ID NO:42:

AACCGAAGGT TCTTGGGTTG AAGAAGGTTT GGTATTCAGA GGTAGCGGTT CTCTTGTCCA    60

(2) INFORMATION FOR SEQ ID NO:43:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (v i i) IMMEDIATE SOURCE:
        (B) CLONE: ZC1629

(x i) SEQUENCE DESCRIPTION: SEQ ID NO:43:

CTAGACTATT CACCGAATT    19

(2) INFORMATION FOR SEQ ID NO:44:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (v i i) IMMEDIATE SOURCE:
        (B) CLONE: ZC1630

(x i) SEQUENCE DESCRIPTION: SEQ ID NO:44:

GATCAATTCG GTGAATAGT    19

(2) INFORMATION FOR SEQ ID NO:45:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (v i i) IMMEDIATE SOURCE:
        (B) CLONE: ZC5339

(x i) SEQUENCE DESCRIPTION: SEQ ID NO:45:

AGCTGCTTGG ACAAGAGATC CTCCACGGCT ACGGATGTGT TCTGGGCCAA GTACACAGCT    60

TGTGAGACAG CGAGGACGCC    80

(2) INFORMATION FOR SEQ ID NO:46:

-continued (i) SEQUENCE CHARACTERISTICS:
  (A) LENGTH: 80 base pairs
  (B) TYPE: nucleic acid
  (C) STRANDEDNESS: single
  (D) TOPOLOGY: linear (vii) IMMEDIATE SOURCE:
  (B) CLONE: ZC5340

(xi) SEQUENCE DESCRIPTION: SEQ ID NO:46:

TCGAGGCGTC CTCGCTGTCT CACAAGCTGT GTACTTGGCC CAGAACACAT CCGTAGCCGT         60

GGAGGATCTC TTGTCCAAGC         80

(2) INFORMATION FOR SEQ ID NO:47:

(i) SEQUENCE CHARACTERISTICS:
  (A) LENGTH: 90 base pairs
  (B) TYPE: nucleic acid
  (C) STRANDEDNESS: single
  (D) TOPOLOGY: linear (vii) IMMEDIATE SOURCE:
  (B) CLONE: ZC5344

(xi) SEQUENCE DESCRIPTION: SEQ ID NO:47:

AGCTTGGACA AGAGATCCGA AGGCTCCAGT GTGAATCTGT CACCTCCATT GGAGCAGTGT         60

GTCCCTGATC GGGGGCAGCA GTACCAGGGG         90

(2) INFORMATION FOR SEQ ID NO:48:

(i) SEQUENCE CHARACTERISTICS:
  (A) LENGTH: 88 base pairs
  (B) TYPE: nucleic acid
  (C) STRANDEDNESS: single
  (D) TOPOLOGY: linear (vii) IMMEDIATE SOURCE:
  (B) CLONE: ZC5345

(xi) SEQUENCE DESCRIPTION: SEQ ID NO:48:

CGCCCCTGGT ACTGCTGCCC CCGATCAGGG ACACACTGCT CCAATGGAGG TGACAGATTC         60

ACACTGGAGC CTTCGGATCT CTTGTCCA         88

METHODS FOR PRODUCING THROMBIN

RELATED APPLICATIONS

The present application is a continuation-in-part of Ser. No. 07/860,701, now abandoned, filed Mar. 31, 1992, which is a continuation-in-part of Ser. No. 07/816,281, now abandoned, filed Dec. 31, 1991, the disclosures of which are incorporated herein by reference.

FIELD OF THE INVENTION

The present invention is directed generally toward methods for producing recombinant proteins, and more specifically, to methods for producing thrombin from host cells through the use of recombinant DNA techniques.

BACKGROUND OF THE INVENTION

The penultimate step of the coagulation cascade is the Factor Xa-complex-catalyzed conversion of prothrombin to thrombin. Prothrombin is a single-chain, vitamin K-dependent glycoprotein that is synthesized in the liver. Prothrombin contains a pro peptide, a gla domain, two kringle regions, an A chain and a serine protease domain. The A chain is disulfide-linked to the serine protease domain. Conversion to thrombin requires that prothrombin be cleaved in two places by Factor Xa-complex. One factor Xa cleavage liberates a protein fragment comprising the gla domain and two kringle regions. The other factor Xa cleavage, which is responsible for producing a catalytically active molecule, cleaves the A chain from the serine protease domain to form a disulfide-linked two chain protein. Cleavages at both factor Xa cleavage sites result in the formation of active thrombin which is composed of the 49 amino acid A chain disulfide-bonded to the serine protease domain. Thrombin hydrolyses specific arginyl-glycine bonds in fibrinogen to produce fibrin monomers, which self-assemble into a fibrin clot, and in Factor XIII to produce Factor XIIIa, which in turn cross-links the fibrin monomers to strengthen and stabilize the fibrin clot. The role of thrombin in the coagulation cascade has been reviewed, for example by Jackson and Nemerson (*Ann. Rev. Biochem.* 49: 765–811 (1980)).

Thrombin is used clinically to control bleeding during surgery, for burns and in certain trauma situations (Nakamura et al. *The Amer. Surgeon* 57:226–230 (1991); Thompson et al. *Ophthalmology* 93:279–282 (1986); Harris et al., *J. Bone Joint Surg.* [Am] 60:454–456 (1978); Craig and Asher, *Spine* 2:313–317 (1977); Prasad et al. *Burns* 17:70–71 (1991)). Bovine thrombin is also a component of some commercial tissue glues.

Commercial thrombin therapeutics are purified from pooled human and animal blood products and as such run the risk of contamination with viruses such as the HIV and hepatitis viruses. In comparing three commercial thrombin preparations, Suzuki and Sakuragawa (*Thromb. Res.* 53:271–278, 1989) found that the preparations contained contaminating proteins, and the human preparation contained immunoglobulin G, hepatitis B surface antigen antibodies and human immunodeficiency antibodies. Xenogeneic immunization with bovine thrombin has been reported in patients who have developed self-reactive antibodies to both human thrombin and human factor V (factor V is a contaminant in the bovine thrombin preparation) (Stricker et al., *Blood* 72:1375–1380 (1988); Flaherty and Weiner, *Blood* 73:1388 (1989); Flaherty et al., *Ann Int. Med.* 111:631–634 (1989); Zehnder and Leung, *Blood* 76:2011–2016 (1990); Lawson et al., *Blood* 76:2249–2257 (1990); Stricker et al., *Blood* 72:1375–1380 (1988); Berguer et al., *J. Trauma* 31:408–411 (1991)). In addition, concerns have recently been raised regarding the possible contamination of bovine products with pathogens such as the bovine spongeform encephalitis agent, which is not detectable or inactivatable by conventional means. Therapeutic human blood products are also subject to contamination by viral particles such as the hepatitis virus and the human immunodeficiency virus.

Although prothrombin has been prepared through recombinant means, approximately 14% of the protein was abnormally carboxylated.

There is therefore a need in the art for methods for producing thrombin that is essentially free of contaminating proteins. The present invention fulfills this need and provides other related advantages.

SUMMARY OF THE INVENTION

Briefly stated, the present invention provides methods for producing thrombin. In one aspect, the methods comprise a) introducing into a host cell a DNA construct capable of directing the expression of a thrombin precursor and comprising the following operably linked elements: a transcriptional promoter, a DNA sequence encoding a gla-domainless prothrombin and a transcriptional terminator; b) growing the host cell under suitable conditions to allow the expression of the thrombin precursor encoded by the DNA sequence of step a; and c) isolating the thrombin precursor from the host cell. In one embodiment of the invention, the thrombin precursors are secreted from the host cell. In another aspect of the invention, the thrombin precursors are activated in vivo or may be activated in vitro.

In one embodiment of the invention, the gla-domainless prothrombin comprises kringle 1, kringle 2, the A chain, an activation site and the serine protease domain of prothrombin. In another embodiment of the invention, the gla-domainless prothrombin comprises kringle 2, the A chain, an activation site and the serine protease domain of prothrombin. In yet another embodiment of the invention, the gla-domainless prothrombin comprises the A chain, an activation site and the serine protease domain of prothrombin.

DESCRIPTION OF THE SPECIFIC EMBODIMENTS

Figure 1:
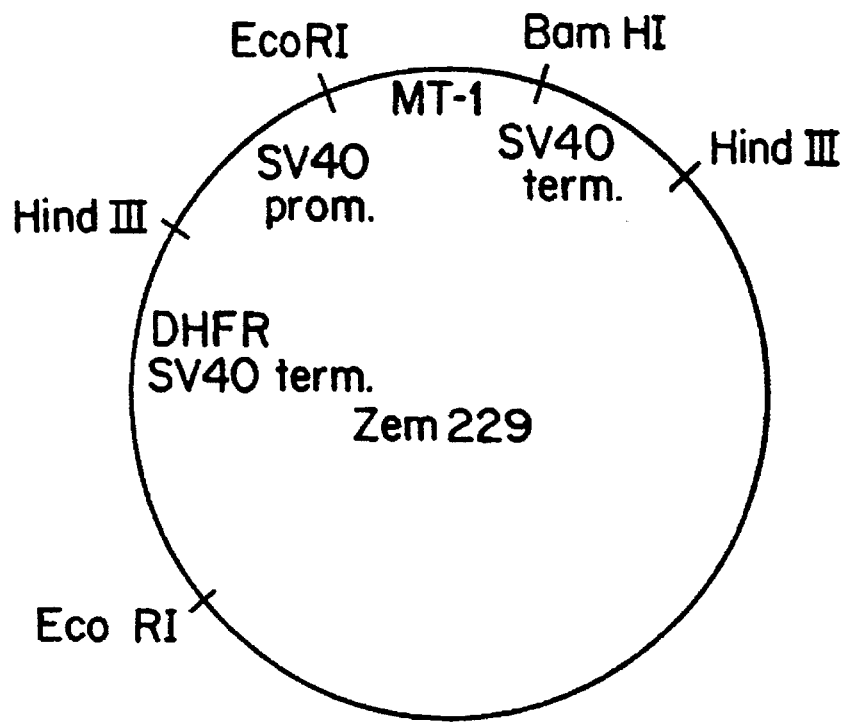
FIG. 1 illustrates the construction of plasmid Zem229R. Symbols used are SV40 term., SV40 terminator; DHFR, dihydrofolate reductase cDNA; SV40 prom., SV40 promoter; MT-1, mouse metallothionien-1 promoter.
Figure 1:
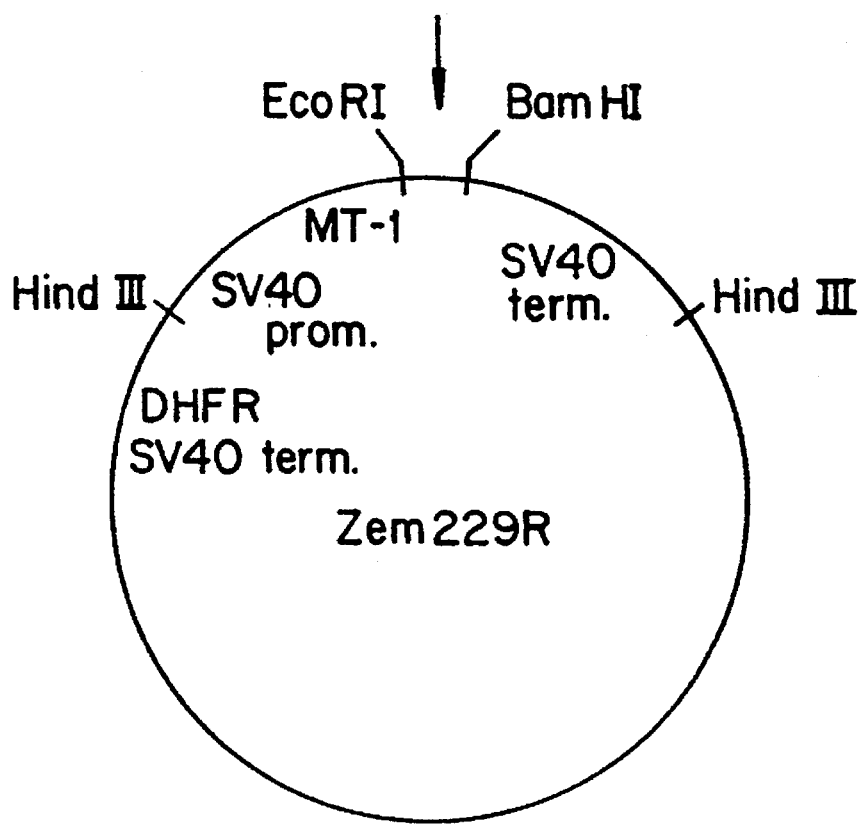

Prior to setting forth the invention, it may be helpful to an understanding thereof to set forth definitions of certain terms to be used hereinafter.

Signal Sequence

A DNA segment encoding a secretory peptide. Signal sequences may also be called leader sequences, prepro sequences and/or pre sequences. A secretory peptide is an amino acid sequence that acts to direct the secretion of a mature polypeptide or protein from a cell. Secretory peptides are characterized by a core of hydrophobic amino acids and are typically (but not exclusively) found at the amino termini of newly synthesized proteins. The secretory peptide may be divided into domains, including a signal peptide domain and a C-terminal domain. Such domains may be interrupted by the mature coding region of a protein. A DNA segment encoding the third domain of the yeast Barrier protein, for example, may be positioned in proper reading frame relative to the BAR1 signal peptide and the DNA sequence of interest either immediately 3' or 5' to the DNA sequence of interest. Very often the secretory peptide is cleaved from the mature protein during secretion. Such secretory peptides contain processing sites that allow cleavage of the secretory peptide from the mature protein as it passes through the secretory pathway. Processing sites may be encoded within the secretory peptide or may be added to the peptide by, for example, in vitro mutagenesis.

Pro sequence

A DNA segment which encodes a propeptide and functions to direct or signal the processing of a protein or peptide. The propeptides of vitamin K-dependent glycoproteins are highly conserved. The most strongly conserved amino acids in the propeptides are the Val-Phe at positions −17 and −16, Glu or Gln at −12, Ala at −10, Val-Leu at −7 and −6, Arg at −4 and Lys-Arg at −2 and −1 (Foster et al., *Biochemistry* 26:7003–7011 (1987)). Pro sequences are generally preceded by a pre sequence and are removed from the protein during processing and secretion.

For vitamin K-dependent glycoproteins, the pro peptide is believed to ensure proper post-translational processing (e.g., gamma-carboxylation of glutamic acid residues in the Gla domain) of the protein.

Gla Domain

An amino acid sequence, generally containing from about 26 to about 45 amino acids, generally but not always located in the amino terminal region of a protein, that contains between three and twelve glutamyl residues that are post-translationally modified to γ-carboxyglutamyl residues (Gla). In some cases, the Gla domain may be defined by exon-intron boundaries of the genomic sequence. The γ-carboxyglutamyl residues in Gla domains facilitate the calcium-mediated binding of vitamin K-dependent proteins to membrane phospholipids. However, prothrombin, which has a gla domain that is encoded within Exon II of the genomic sequence, does not require the gla domain for biological activity. In the absence of a functional gla domain, a gla-domainless prothrombin has a $K_m$ of activation by the Factor Xa complex that is markedly higher than wild-type prothrombin. Assays for determining prothrombin activation have been described, for example, by Malhorta et al. (*J. Biol. Chem.* 260:279–287 (1983); which is incorporated by reference herein) or Blanchard et al. (*J. Lab. Clin. Med.* 101:212–255 (1983); which is incorporated by reference herein).

Gla-domainless Prothrombin

A polypeptide having, upon activation, the activity of thrombin. A gla-domainless prothrombin is a single polypeptide that lacks a functional gla domain and comprises at least a portion of the A chain joined to the serine protease domain and contains a disulfide-bond between the A chain and the serine protease domain.

Thrombin

A two chain, disulfide-bonded, glycosylated polypeptide that cleaves specific bonds in fibrinogen to produce fibrin monomers that self-assemble to form a fibrin clot. As disclosed in more detail herein, prothrombin is activated to thrombin by two Factor Xa-complex cleavages (between Arginine, amino acid 307 and Threonine, amino acid 308 of Sequence ID Numbers 2 and 3 to remove the gla and kringle domains and between Arginine, amino acid 356 and Isoleucine, amino acid 356 of Sequence ID Numbers 2 and 3 to cleave the A chain from the serine protease domain). The A chain and the serine protease domains are generally regarded as being bounded by these Factor Xa cleavage sites. However, as will be evident to one skilled in the art, allelic variations and other deletions, additions or minor amino acid changes in the A chain and serine protease domains that do not destroy thrombin activity are encompassed within the present invention. The term "activation site" refers to the proteolytic cleavage site between the A chain and the serine protease domain, cleavage of which results in the activation of prethrombin to active thrombin. In the case of native prothrombin and prethrombin, the wild-type thrombin activation site is a Factor Xa cleavage site.

Expression Vector

A DNA molecule which contains, inter alia, a DNA sequence encoding a protein of interest together with a promoter and other sequences, such as a transcription terminator and polyadenylation signal, that facilitate expression of the protein. Expression vectors further contain genetic information that provides for their replication in a host cell, either by autonomous replication or by integration into the host genome. It will be evident to one skilled in the art that such information that provides for the autonomous replication of an expression vector in a host cell encompasses known yeast and bacterial origins of replication. As is discussed in more detail herein, suitable yeast vectors contain both a yeast origin of replication and a bacterial origin of replication, and bacterial and mammalian vectors generally contain a bacterial origin of replication. Examples of expression vectors commonly used for recombinant DNA are plasmids and certain viruses, although they may contain elements of both. They also may include one or more selectable markers.

Transfection or transformation

The process of stably and hereditably altering the genotype of a recipient cell or microorganism by the introduction of purified DNA. This is typically detected by a change in the phenotype of the recipient organism. The term "transformation" is generally applied to microorganisms, while "transfection" is used to describe this process in cells derived from multicellular organisms.

Cultured cell

A cell capable of being grown in liquid or solid media over a number of generations. In the case of cells derived from multicellular organisms, a cultured cell is a cell isolated from the organism as a single cell, a tissue, or a portion of a tissue.

DNA Construct

A DNA molecule, or a clone of such a molecule, either single or double-stranded, which has been modified through human intervention to contain segments of DNA combined and juxtaposed in a manner that would not otherwise exist in nature. DNA constructs may contain operably linked elements which direct the transcription and translation of DNA sequence encoding polypeptides of interest. Such elements include promoters, enhancers and transcription terminators. By virtue of the elements contained within the DNA constructs, certain constructs are understood to be capable of directing the expression and/or secretion of the encoded polypeptides. If a DNA sequence encoding a polypeptide of interest contains a secretory signal sequence, the DNA construct containing appropriate elements will be considered to be capable of directing the secretion of the polypeptide.

As noted above, prothrombin is normally produced as a single-chain, glycosylated, gamma-carboxylated protein that contains a gla domain, first and second kringle domains, an A chain and a serine protease domain. The A chain, also known as the light chain, is disulfide-bonded to the serine protease domain, which is known as both the B chain and the catalytic domain. During the coagulation cascade prothrombin is cleaved in two places by the Factor Xa-complex, resulting in the liberation of thrombin. One Factor Xa-complex cleavage of prothrombin liberates the gla and kringle domains of prothrombin. The second Factor Xa-complex cleaves the prothrombin at the activation site, splitting the A chain from the serine protease domain to produce thrombin.

An object of the present invention is to provide methods for producing thrombin using recombinant methods and eukaryotic host cells. A feature of the present invention is the use of an expression vector comprising a DNA sequence encoding gla-domainless prothrombin. An additional feature of the present invention is the use of the expression vectors within host cells to produce thrombin precursors that are activated either in vivo or in vitro to thrombin.

The gla domain of prothrombin may be rendered nonfunctional by removal of part or all of the gla domain by conventional methods. Alternatively, the sequences encoding glutamyl residues within the gla domain may be deleted or may be altered to result in amino acid substitution. The kinetics of activation of prothrombin variants having altered gla domains may be assessed using the method essentially described by Malhorta et al. (ibid.), as described below. Proteins that do not contain functional gla domains have $K_m$'s of activation that are generally about 15 times higher than that of wild-type prothrombin, preferably about 20 times higher. Within one embodiment of the invention, gla-domainless prothrombins described herein are activated prior to utilization in vivo.

The activation kinetics of prothrombin variants having altered domains may be determined as follows. Briefly, a solution containing 1.4 μM to 6.5 μM of the prothrombin variant in 5 mM $CaCl_2$ is incubated at 22° C. for longer than 10 minutes. After incubation, a solution containing Factor Xa, Factor Va, $CaCl_2$, phosphatidylcholine-phosphatidylserine (3:1) (referred to hereinafter as PCPS), and dansyl 5-dimethylaminonaphthalene-1-sulfonyl (referred to hereinafter as DAPA) is added such that the final concentrations of the 2.0 ml reaction mixtures are 0.03 M Tris-HCl, pH 7.4; 0.10M NaCl; 3.0 nM Factor Xa; 10.0 nM Factor Va; 30 μM PCPS; 5.0 mM $CaCl_2$ and 10 μM DAPA. At the same time, a positive control containing 1.4 μM to 6.5 μM prothrombin in 5 mM $CaCl_2$ is incubated at 22° C. for longer than 10 minutes. After incubation, 25 μl of a solution containing Factor Xa; Factor Va; $CaCl_2$; PCPS; and DAPA is added such that the final concentrations of the 2.0 ml reaction mixtures are 0.03M Tris-HCl, pH 7.4; 0.10 M NaCl 0.5 nM Factor Xa; 10.0 nM Factor Va; 30 μM PCPS; 5.0 mM $Ca^{2+}$ and 10 μM DAPA. The reaction progress is monitored by measuring the fluorescent intensity of the DAPA-thrombin complex, using an excitation wavelength of 345 nm and an emission wavelength of 545 nm with a 430 nm cutoff filter used in the emission beam. The excitation and emission slit widths are 10 nm and 15 nm, respectively. The $K_m$ and $k_{cat}$ are determined by analyzing the reaction profile according to the integrated Michaelis-Menten-Henri procedure (Nesheim et al., *J. Biol. Chem.* 254:10952–10962 (1979); which is incorporated by reference herein).

Within certain embodiments of the invention, the wild-type thrombin activation site is altered in such a way as to allow the thrombin precursors to be activated in vivo or to be activated autocatalytically. For example, the wild-type thrombin activation site can be altered in such a way that it can be cleaved by the *Saccharomyces cerevisiae* KEX2 gene product. The KEX2 gene encodes an endopeptidase that cleaves after a dibasic amino acid sequence (Fuller et al., in Leive, ed., *Microbiology:* 1986, 273–278 (1986)). Preferably, the KEX2 cleavage site is encoded by the amino acid sequence KR. More preferably, the KEX2 cleavage site is encoded by the amino acid sequence RRKR (Sequence ID No. 34) or LDKR (Sequence ID No. 35). A host cell line that is thus capable of expressing the KEX2 gene is thus capable of cleaving thrombin precursors containing a KEX2 site at the activation site to produce thrombin. Host cells that do not naturally express KEX2 may be transformed or transfected with the *Saccharomyces cerevisiae* KEX2 gene as described by, for example, Mulvihill et al. (co-pending U.S. patent application Ser. No. 07/445,302, which is incorporated by reference herein in its entirety) and Mulvihill et al., EP 319,944. Alternatively, the wild-type thrombin activation site may be altered in such a way as to render the resulting proteins cleavable by thrombin. In a preferred embodiment, the thrombin cleavage site is encoded by the amino acid sequence PR. Such a change allows the thrombin precursors to be activated autocatalytically following a minute addition of exogenous thrombin. In one embodiment of the invention, the wild-type thrombin activation site is replaced with a copy of mature α-factor flanked on the 5' end with a thrombin cleavage site and on the 3' end with a KEX2 cleavage site. Such alterations at the activation site may be obtained using the techniques of, for example, adapter technology, in vitro mutagenesis and polymerase chain reaction (PCR) mutagenesis.

DNA segments encoding gla-domainless prothrombins may be produced synthetically or may be prepared from DNA segments encoding prothrombin cloned from, for example, human liver cells (Degen et al, *Biochemistry* 22:2087–2097 (1983) and Degen and Davie, *Biochemistry* 26:6165–6177 (1987)) or from bovine liver essentially as described by MacGillivray and Davie, *Biochemistry* 23:1626–1634 (1984), which are incorporated herein by reference, using cloning methods such as those described by Maniatis et al. (*Molecular Cloning: A Laboratory Manual*, Cold Spring Harbor, N.Y. (1982)), Sambrook et al. (*Molecular Cloning: A Laboratory Manual*, 2d Ed., Cold Spring Harbor, N.Y. (1989)) or Mullis et al. (U.S. Pat. No. 4,683,195), each of which is incorporated herein by reference. DNA segments encoding prothrombin may be altered to produce the DNA segments encoding gla-domainless prothrombin of the present invention by restriction digestion and religation, in vitro mutagenesis or by mutagenesis using polymerase chain reaction amplification.

A representative nucleotide sequence encoding human prothrombin and the deduced amino acid sequence is shown in Sequence ID Nos. 2 and 3. As will be evident to one skilled in the art, DNA segments encoding gla-domainless prothrombins encompass allelic variants and genetically engineered or synthetic variants that contain conservative amino acid substitutions and/or minor additions, substitutions or deletions of amino acids. DNA sequence variants also encompass degeneracies in the DNA code wherein other codons, including host-preferred codons, are substituted for the analogous codons in the wild-type sequence. DNA segments comprising DNA sequences capable of hybridizing to the DNA sequences of the present invention under high or low stringency (see Sambrook et al., ibid.) and DNA segments encoding sequences that are degenerate as a result of the genetic code to the amino acid sequences of the present invention are encompassed within the present invention. Genetically engineered variants may be obtained by using oligonucleotide-directed site-specific mutagenesis, by use of restriction endonuclease digestion and adapter ligation, or other methods well established in the literature (see, e.g., Sambrook et al., ibid. and Smith et al., *Genetic Engineering: Principles and Methods*, Plenum Press, 1981; which are incorporated herein by reference).

DNA segments encoding gla-domainless prothrombin are inserted into suitable expression vectors which are in turn introduced into appropriate host cells. Expression vectors for use in carrying out the present invention comprise a promoter capable of directing the transcription of a cloned DNA, a DNA segment encoding a gla-domainless prothrombin, and a transcriptional terminator.

To direct proteins of the present invention into the secretory pathway of the host cell, at least one signal sequence is operably linked to the DNA sequence of interest. Preferred signals include the alpha factor signal sequence (pre-pro sequence; Kurjan and Herskowitz, *Cell* 30:933–943 (1982); Kurjan et al., U.S. Pat. No. 4,546,082; Brake, U.S. Pat. No. 4,870,008), the PHO5 signal sequence (Beck et al., WO 86/00637), the BAR1 secretory signal sequence (MacKay et al., U.S. Pat. No. 4,613,572; MacKay, WO 87/002670), the SUC2 signal sequence (Carlson et al., *Mol. Cell. Biol.* 3: 439–447 (1983)), the α-1-antitrypsin signal sequence (Kurachi et al., *Proc. Natl. Acad. Sci. USA* 78: 6826–6830 (1981)), the α-2 plasmin inhibitor signal sequence (Tone et al., *J. Biochem.* (Tokyo) 102:1033–1042 (1987)) and the tissue plasminogen activator leader sequence (Pennica et al., *Nature* 301:214–221 (1983)). Alternatively, a secretory signal sequence may be synthesized according to the rules established, for example, by von Heinje (*Eur. J. Biochem.* 133: 17–21 (1983); *J. Mol. Biol.* 184: 99–105, (1985); *Nuc. Acids Res.* 14:4683–4690 (1986)).

Signal sequences may be used singly or may be combined. For example, a first signal sequence may be used singly or in combination with a sequence encoding the third domain of Barrier (described in U.S. Pat. 5,037,743, incorporated by reference herein in its entirety). A DNA segment encoding the third domain of Barrier may be positioned in proper reading frame 3' of the DNA sequence of interest or 5' to the DNA sequence and in proper reading frame with both the signal sequence and the DNA sequence of interest.

Host cells for use in practicing the present invention include mammalian, avian, plant, insect, fungal and bacterial cells. Fungal cells, including species of yeast (e.g., Saccharomyces spp., Schizosaccharomyces spp.) or filamentous fungi (e.g., Aspergillus spp., Neurospora spp.) may be used as host cells within the present invention. Strains of the yeast *Saccharomyces cerevisiae* are particularly preferred.

Suitable yeast vectors for use in the present invention include YRp7 (Struhl et al., *Proc. Natl. Acad. Sci. USA* 76:1035–1039 (1978)), YEp13 (Broach et al., *Gene* 8: 121–133 (1979)), POT vectors (Kawasaki et al, U.S. Pat. No. 4,931,373, which is incorporated by reference herein), pJDB249 and pJDB219 (Beggs, *Nature* 275:104–108 (1978)) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al., ibid.), URA3 (Botstein et al., *Gene* 8:17 (1979)), HIS3 (Struhl et al., ibid.) or POT1 (Kawasaki et al., ibid.). Another suitable selectable marker is the CAT gene, which confers chloramphenicol resistance on yeast cells.

Preferred promoters for use in yeast include promoters from yeast glycolytic genes (Hitzeman et al., *J. Biol. Chem.* 255:12073–12080 (1980); Alber and Kawasaki, *J. Mol. Appl. Genet.* 1:419–434 (1982); Kawasaki, U.S. Pat. No. 4,599,311) or alcohol dehydrogenase genes (Young et al., in *Genetic Engineering of Microorganisms for Chemicals*, Hollaender et al., (eds.), p. 355, Plenum, N.Y. (1982); Ammerer, *Meth. Enzymol.* 101: 192–201 (1983)). In this regard, particularly preferred promoters are the TPI1 promoter (Kawasaki, U.S. Pat. No. 4,599,311, 1986) and the ADH2–4$^c$ promoter (Russell et al., *Nature* 304:652–654 (1983); Irani and Kilgore, U.S. patent application Ser. No. 07/631,763, and EP 284,044, which are incorporated herein by reference). The expression units may also include a transcriptional terminator. A preferred transcriptional terminator is the TPI1 terminator (Alber and Kawasaki, ibid.).

In addition to yeast, proteins of the present invention can be expressed in filamentous fungi, for example, strains of the fungi Aspergillus (McKnight et al., U.S. Pat. No. 4,935,349, which is incorporated herein by reference). Examples of useful promoters include those derived from *Aspergillus nidulans* glycolytic genes, such as the ADH3 promoter (McKnight et al., *EMBO J.* 4:2093–2099 (1985)) and the tpiA promoter. An example of a suitable terminator is the ADH3 terminator (McKnight et al., ibid.). The expression units utilizing such components are cloned into vectors that are capable of insertion into the chromosomal DNA of Aspergillus.

Techniques for transforming fungi are well known in the literature, and have been described, for instance, by Beggs (ibid.), Hinnen et al. (*Proc. Natl. Acad. Sci. USA* 75: 1929–1933 (1978)), Yelton et al. (*Proc. Natl. Acad. Sci. USA* 81:1740–1747 (1984)), and Russell (*Nature* 301:167–169 (1983)). The genotype of the host cell will generally contain a genetic defect that is complemented by the selectable marker present on the expression vector. Choice of a particular host and selectable marker is well within the level of ordinary skill in the art.

It may be preferable to use a yeast host cell that contains a genetic deficiency in at least one gene required for asparagine-linked glycosylation of glycoproteins is used. Preferably, the yeast host cell contains genetic deficiencies in either the MNN9 gene or the MNN1 gene or both (described in pending U.S. patent application Ser. No. 189,547 and EP 314,096, which are incorporated by reference herein in their entirety). Most preferably, the yeast host cell contains a disruption of both the MNN1 and MNN9 genes. Yeast host cells having such defects may be prepared using standard techniques of mutation and selection. Ballou et al. (*J. Biol. Chem.* 255: 5986–5991 (1980)) have described the isolation of mannoprotein biosynthesis mutants that are defective in genes which affect asparagine-linked glycosylation. Briefly, mutagenized yeast cells were screened using fluoresceinated antibodies directed against the outer mannose chains present on wild-type yeast. Mutant cells that did not bind antibody were further characterized and were found to be defective in the addition of asparagine-linked oligosaccharide moieties. To optimize production of the heterologous proteins, it is preferred that the host strain carries a mutation, such as the yeast PEP4 mutation (Jones, *Genetics* 85:23–33 (1977)), which results in reduced proteolytic activity. To optimize secretion of the heterologous proteins, it is preferred that the host strain carries a mutation in the PMR1 gene (Smith, U.S. Pat. No. 5,057,416) which results in the increase in secretion of heterologous proteins. It may be advantageous to disrupt the PMR1 gene.

In addition to fungal cells, cultured mammalian cells may be used as host cells within the present invention. Preferred cultured mammalian cells for use in the present invention include the COS-1 (ATCC CRL 1650), BHK, and 293 (ATCC CRL 1573; Graham et al., *J. Gen. Virol.* 6:59–72 (1977)) cell lines. A preferred BHK cell line is the BHK 570 cell line (deposited with the American Type Culture Collection under accession number CRL 10314). In addition, a number of other mammalian cell lines may be used within the present invention, including Rat Hep I (ATCC CRL 1600), Rat Hep II (ATCC CRL 1548), TCMK (ATCC CCL 139), Human lung (ATCC CCL 75.1), Human hepatoma (ATCC HTB-52), Hep G2 (ATCC HB 8065), Mouse liver (ATCC CCL 29.1), NCTC 1469 (ATCC CCL 9.1) and DUKX cells (Urlaub and Chasin, *Proc. Natl. Acad. Sci USA* 77: 4216–4220 (1980)).

Mammalian expression vectors for use in carrying out the present invention will include a promoter capable of directing the transcription of a cloned gene or cDNA. Preferred promoters include viral promoters and cellular promoters. Viral promoters include the immediate early cytomegalovirus promoter (Boshart et al., *Cell* 41:521–530 (1985)) and the SV40 promoter (Subramani et al., *Mol. Cell. Biol.* 1:854–864 (1981)). Cellular promoters include the mouse metallothionein-1 promoter (Palmiter et al., U.S. Pat. No. 4,579,821), a mouse $V_\kappa$ promoter (Bergman et al., *Proc. Natl. Acad. Sci. USA* 81:7041–7045 (1983); Grant et al., *Nuc. Acids Res.* 15:5496 (1987)) and a mouse $V_H$ promoter (Loh et al., *Cell* 33:85–93 (1983)). A particularly preferred promoter is the major late promoter from Adenovirus 2 (Kaufman and Sharp, *Mol. Cell. Biol.* 2:1304–13199 (1982)). Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730 (1981)). The expression vectors may include a noncoding viral leader sequence, such as the Adenovirus 2 tripartite leader, located between the promoter and the RNA splice sites. Preferred vectors may also include enhancer sequences, such as the SV40 enhancer and the mouse μ enhancer (Gillies, *Cell* 33: 717–728 (1983)). Expression vectors may also include sequences encoding the adenovirus VA RNAs.

Cloned DNA sequences may be introduced into cultured mammalian cells by, for example, calcium phosphate-mediated transfection (Wigler et al., *Cell* 14: 725 (1978); Corsaro and Pearson, *Somatic Cell Genetics* 7: 603 (1981); Graham and Van der Eb, *Virology* 52:456 (1973); which are incorporated by reference herein in their entirety). Other techniques for introducing cloned DNA sequences into mammalian cells, such as electroporation (Neumann et al., *EMBO J.* 1:841–845 (1982)), may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is the DHFR gene. Selectable markers are reviewed by Thilly (*Mammalian Cell Technology*, Butterworth Publishers, Stoneham, Mass., which is incorporated herein by reference). The choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture which is introduced into the cells.

Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Preferred prokaryotic host cells for use in carrying out the present invention are strains of the bacteria *Escherichia coli*, although Bacillus and other genera are also useful. Techniques for transforming these hosts and expressing foreign genes cloned in them are well known in the art (see e.g., Maniatis et al. and Sambrook et al., ibid.). Vectors used for expressing foreign genes in bacterial hosts will generally contain a selectable marker, such as a gene for antibiotic resistance, and a promoter which functions in the host cell. Appropriate promoters including the trp (Nichols and Yanofsky, *Meth. Enzymol.* 101:155–164 (1983)), lac (Casadaban et al., *J. Bacteriol.* 143:971–980 (1980)), and phage λ promoter systems (Queen, *J. Mol. Appl. Genet.* 2:1–10 (1983)). Plasmids useful for transforming bacteria include pBR322 (Bolivar et al., *Gene* 2:95–113 (1977)), the pUC plasmids (Messing, *Meth. Enzymol.* 101:20–77 (1983), Vieira and Messing, *Gene* 19:259–268 (1982)), pCQV2 (Queen, ibid.), and derivatives thereof. Plasmids may contain both viral and bacterial elements. Methods for the recovery of the proteins in biologically active form are discussed in U.S. Pat. Nos. 4,966,963 and 4,999,422, which are incorporated herein by reference.

Promoters, terminators and methods useful for introducing expression vectors encoding gla-domainless prothrombin of the present invention into plant, avian and insect cells have been described in the art. The use of baculoviruses, for example, as vectors for expressing heterologous DNA sequences in insect cells has been reviewed by Atkinson et al. (*Pestic. Sci.* 28:215–224 (1990)). The use of *Agrobacterium rhizogenes* as vectors for expressing genes in plant cells has been reviewed by Sinkar et al. (*J. Biosci. (Banglaore)* 11:47–58 (1987)).

Host cells containing DNA constructs of the present invention are then cultured to produce gla-domainless prothrombin. The cells are cultured according to standard methods in a culture medium containing nutrients required for growth of the host cells. A variety of suitable media are known in the art and generally include a carbon source, a nitrogen source, essential amino acids, vitamins, minerals and growth factors. The growth medium will generally select for cells containing the DNA construct by, for example, drug selection or deficiency in an essential nutrient which is complemented by the selectable marker on the DNA construct or co-transfected with the DNA construct.

Yeast cells, for example, are preferably cultured in a chemically defined medium, comprising a non-amino acid nitrogen source, inorganic salts, vitamins and essential amino acid supplements. The pH of the medium is preferably maintained at a pH greater than 2 and less than 8, preferably at pH 6.5. Methods for maintaining a stable pH include buffering and constant pH control, preferably through the addition of sodium hydroxide. Preferred buffering agents include succinic acid and Bis-Tris (Sigma, St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1M and 1.5M, preferably at 0.5M or 1.0M. Mammalian cells are generally cultured in commercially available serum-containing or serum-free media. Selection of a medium appropriate for the particular cell line used is within the level of ordinary skill in the art.

Host cells containing DNA constructs of the present invention encoding a gla-domainless prothrombin wherein the factor Xa cleavage site is replaced with a thrombin activation site are preferably cultured in a chemically defined serum-free medium. Serum-free media may be obtained from commercial sources, for example, GIBCO-BRL (Gaithersburg, MD) or may be prepared using recipes well known in the literature and published, for example, by the American Type Culture Collection. Selection of suitable media components is within the level of ordinary skill in the art. It may be preferable to facilitate the activation of certain thrombin precursors produced from these transfectants by the addition of heparin or thrombin. More particularly, the activation of thrombin precursors containing a thrombin cleavage site in place of the wild-type thrombin activation site (Arg-Ile) may be faciliated by the addition of heparin to the medium. Preferably, between 0.5 and 5.0 U/ml of heparin is added to the serum-free medium, more preferably between 1 and 5 U/ml and most preferably 1 U/ml of heparin is added to the serum-free medium. To activate the protein produced from cells containing DNA constructs of the present invention encoding a gla-domainless prothrombin wherein the factor Xa activation site is replaced with a thrombin activation site, between 0.5 and 5 µg/ml of thrombin may be added to the serum-free medium, more preferably between 1 and 2 µg/ml of thrombin, with 1 µg/ml of thrombin added to the serum-free medium being particularly preferred.

Thrombin precursors produced according to the present invention may be purified by conventional chromatography preferably using cibacron blue F3GA dye that has been adhered to a solid matrix such as AFFI-GEL® blue affinity gel (Bio-Rad, Richmond, Calif.). Thrombin precursors may be eluted from the column by exposure to high salt of between 0.6 and 1M NaCl, preferably 1M NaCl. The peak fractions, as determined by measuring the absorbance at 280 nm, are pooled. The pool is diluted in 25 mM Tris, pH 7.4, and the thrombin precursors are activated by the addition of between 1:1,000 and 1:2,000 (w/w) snake venom activator (described in more detail below) based on an estimated protein concentration. The activated material is purified by chromatography preferably using para-aminobenzamidine coupled to a solid matrix such as Benzamidine Sepharose 4B (Pharmacia LKB Biotechnology Inc., Piscataway, N.J.). Thrombin may be eluted from the column by exposure to 15 mM benzamidine. The fractions are assayed for chromogenic activity by diluting aliquots of the fractions and adding a thrombin chromogenic substrate. The pooled fractions may be desalted by applying the material to a G-25 column (Bio-Rad).

It may be advantageous to pre-run the thrombin precursors across a column matrix that has been crosslinked to heparin, such as AFFI-GEL heparin gel (Bio-Rad, Richmond, Calif.) or the like, to remove thrombin and thrombin-like contaminants. Alternatively, thrombin precursors may be purified by affinity chromatography using anti-thrombin antibodies. Other methods of thrombin purification are set forth in U.S. Pat. No. 4,965,203, which is incorporated herein by reference. Activated thrombin produced from gla-domainless prothrombins that are activated in the secretory pathway or are activated in the culture medium may be purified by chromatography using para-aminobenzamidine coupled to a solid matrix as described above.

Purified thrombin precursors may be activated using a venom activator from a viper such as *Echis carnatus* or *Vipera russellii*, preferably from *Echis carnatus* as described by, for example, Teng et al. (*Taxicon.* 27:161–167 (1989)). The *Echis carnatus* activator is preferably purified by sequential chromatography through Sephadex G-150 and DEAE-Sephadex A25 or the like, followed by repetitive FPLC using a Mono Q column. Alternatively, purified thrombin precursors may be activated using Factor Xa essentially as described, for example, by Heldebrant et al. (*J. Biol. Chem.* 248:7149–7163 (1973)), Downing et al. (*J. Biol. Chem.* 250: 8897–8906, (1975)), and Krishnaswamy et al. (*J. Biol. Chem.* 262:3291–3299 (1987)). Thrombin precursors that contain a thrombin activation site may be activated by the addition of thrombin.

Activated material is preferably purified using an S-Sepharose fast flow column and a salt gradient, preferably from 100 mM to 1M. The purified activated material may be further purified by reverse phase HPLC. Additional purification may be achieved by conventional chemical purification means, such as liquid chromatography, gradient centrifugation, and gel electrophoresis, among others. Methods of protein purification are known in the art (see generally, Scopes, R., Protein Purification, Springer-Verlag, N.Y. (1982), which is incorporated herein by reference) and may be applied to the purification of the thrombin precursors described herein. Substantially pure thrombin or thrombin precursors of at least about 50% are preferred, at least about 70–80% more preferred, and 95–99% or more homogeneity most preferred, particularly for pharmaceutical uses. Once purified, partially or to homogeneity as desired, the recombinant thrombin or thrombin precursors may then be used in the preparation of pharmaceutical compositions, etc.

The recombinant human thrombin produced according to the present invention finds a variety of uses, but particularly in pharmaceutical compositions for the treatment of coagulation disorders in mammals, particularly humans. The thrombin preparations of the invention can be used therapeutically as a coagulant or to stabilize clot formation in the repair of wounds, the treatment of bleeding associated with major or minor trauma or surgery, burns, ulcerated lesions, skin grafting, etc. The recombinant thrombin compositions can also be used as components of tissue adhesives, or tissue glues, for example, with preparations of factor XIII or other transglutaminases.

Pharmaceutical compositions of the invention comprise therapeutically effective amounts of recombinant thrombin and an appropriate physiologically acceptable carrier. The pharmaceutical compositions are intended primarily for topical or local administration at the wound or surgical site, etc., but may also be administered intravenously in cases of severe liver failure, major trauma accompanied by excessive bleeding and/or blood replacement regimens, subarachnoid hemorrhage, and the like. Typically the thrombin preparations of the invention can be administered concurrently with other coagulation formulations for increased effectiveness.

A variety of aqueous carriers may be used in formulating the recombinant thrombin pharmaceutical compositions, e.g., buffered water, saline, 0.3% glycine and the like, including glycoproteins for enhanced stability, such as albumin, lipoprotein, fibronectin and/or globulin. The compositions may be sterilized by well known sterilization techniques, and the solutions packaged for use or lyophilized. Other components of the pharmaceutical compositions of the invention can include pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

Other components may also be added to the recombinant thrombin compositions, generally at the time of administration to the patient, to enhance their effectiveness, such as calcium ions, protease inhibitors (e.g., aprotinin), fibrinogen, etc. Admixtures of prostaglandins, other coagulation factors, antihistamines, vasopressins, growth factors, vitamins, antibiotics (e.g., aminoglycosides, penicillins, carbapenems, sulfonamides, tetracyclines) and the like may also be provided. The formulation of various wound tissue adhesives is discussed in detail in U.S. Pat. Nos. 4,427,650, 4,442,655, and 4,655,211, each of which is incorporated herein by reference.

The concentration of therapeutically effective doses of the recombinant human thrombin in the pharmaceutical formulations can vary widely, i.e., from about 100 to about 10,000 NIH standard units (where generally 1 μg of substantially purified thrombin protein equals about 3,000 units), usually at least about 500 to 5,000 units and more preferably from about 1,000 to 2,000 units, and will be selected primarily by volumes, viscosities, strength of the resulting complex, etc., in accordance with the particular use intended, the severity of the wound or bleeding disorder, the mode of administration selected, the general health of the patient, etc. It must be kept in mind that the materials of the present invention may generally be employed in serious disease or injury states, that is, life-threatening or potentially life threatening situations. In such cases, in view of the minimization of extraneous substances, decreased immunogenicity and the prolonged half-life and stability of the recombinant human thrombin made feasible by this invention, it is possible and may be felt desirable by the treating physician to administer substantial excesses of these thrombin compositions.

The following examples are offered by way of illustration, not by way of limitation.

EXAMPLES

Restriction endonucleases and other DNA modification enzymes (e.g., T4 polynucleotide kinase, calf alkaline phosphatase, DNA polymerase I (Klenow fragment), T4 polynucleotide ligase) were obtained from Boehringer Mannheim Biochemicals, Bethesda Research Laboratories (BRL) and New England Biolabs and were used as directed by the manufacturer, unless otherwise noted.

Oligonucleotides were synthesized on an Applied Biosystems Model 380A DNA synthesizer and purified by polyacrylamide gel electrophoresis on denaturing gels. *E. coli* cells were transformed as described by Maniatis et al. (*Molecular Cloning: A Laboratory Manual*, Cold Spring Harbor Laboratory, 1982, incorporated by reference herein) or as described by Sambrook et al. (*Molecular cloning: A Laboratory Manual*, Cold Spring Harbor Laboratory, Second Edition, 1988, incorporated by reference herein). M13 and pUC cloning vectors and host strains were obtained from BRL.

Example 1

Cloning of a Prothrombin cDNA

A cDNA encoding human prothrombin was isolated essentially as described by Degen et al. (*Biochemistry* 22: 2087–2097 (1983); which is incorporated herein in its entirety by reference). Briefly, a cDNA library prepared from human liver RNA was subcloned into the Pst I site of plasmid pBR322. The cDNA library was transformed *E. coli* and approximately 18,000 transformants were screened using a pool of degenerate oligonucleotides having the sequence 5'0 CCNGCRCAR AACAT 3' (Sequence I.D. No. 1). Approximately thirty positive clones were identified. Rescreening of the positive clones with a radiolabeled Ava I-Bam HI restriction fragment from a bovine prothrombin cDNA identified fourteen clones that hybridized to both the degenerate oligonucleotide pool and the bovine prothrombin cDNA. Two of the positive clones were selected for further characterization. One clone was found to contain the complete human prothrombin cDNA sequence. The DNA sequence and deduced amino acid sequence of a human prothrombin cDNA sequence is shown in Sequence I.D. Nos. 2 and 3.

A prothrombin expression vector was constructed using synthetic oligonucleotides designed to encode the prothrombin leader. Synthetic oligonucleotides were designed to form, when annealed, an adapter encoding the human prothrombin leader having a 5' Eco RI adhesive end and a 3' Sst I end. Oligonucleotides ZC1378, ZC1379, ZC1323 and ZC1324 (Sequence ID Nos. 8, 9, 6 and 7, respectively) were kinased and annealed using the method essentially described by Sambrook et al. (ibid., which is incorporated by reference herein in its entirety). The kinased, annealed adapter was ligated with M13mp19 which had been linearized by digestion with Eco RI and Sst I. The ligation mixture was transformed into *E. coli* strain JM101, and single-stranded DNA was prepared for sequence analysis. After sequence analysis identified a clone containing the correct sequence, RF DNA was prepared from the clone and digested with Eco RI and Sst I to isolate the 160 bp fragment. The leader-containing fragment was ligated to a partial Sst I-Eco RI fragment encoding a portion of a protein C cDNA obtained from plasmid p594 and Eco RI-linearized, bacterial alkaline phosphatased pDX (plasmids p594 and pDX are described in commonly assigned U.S. Pat. No. 4,959,318, which is incorporated herein by reference). The ligation mixture was transformed into *E. coli* strain JM101, and plasmid DNA was prepared from selected transformants. Restriction analysis identified a clone having the fragments in the correct orientation relative to the promoter. The prothrombin leader was obtained by digesting the plasmid with Eco RI and Apa LI to isolate the 756 base pair fragment.

The remainder of the prothrombin coding sequence was obtained from the initial cDNA clone which was digested with Apa LI and Bam HI to isolate the 1558 base pair fragment and with Bam I and Pst I to isolate the 385 base pair fragment. Synthetic oligonucleotides ZC2490 and ZC2492 (Sequence ID Nos. 10 and 11) were designed to form, when annealed, a Pst I-Eco RI adapter to join the 3' end of the prothrombin cDNA with the Zem229R expression vector.

Plasmid Zem229 is a pUC18-based expression vector containing a unique Bam HI site for insertion of cloned DNA between the mouse metallothionein-1 promoter and SV40 transcription terminator and an expression unit containing the SV40 early promoter, mouse dihydrofolate reductase gene, and SV40 terminator. Zem229 was modified to delete the two Eco RI sites by partial digestion with Eco RI, blunting with DNA polymerase I (Klenow fragment) and dNTPs, and re-ligation. Digestion of the resulting plasmid with Bam HI followed by ligation of the linearized plasmid with Bam HI-Eco RI adapters resulted in a unique Eco RI cloning site. The resultant plasmid was designated Zem229R (FIG. 1).

The Eco RI-Apa LI prothrombin leader fragment, the 1.5 kb Apa LI-Bam HI prothrombin coding sequence fragment, the 0.385 kb Bam HI-Pst I prothrombin coding sequence fragment and the Pst I-Eco RI adapter were ligated with Eco RI-linearized Zem229. The ligation mixture was transformed into *E. coli*, and plasmid DNA was prepared from selected transformants. Restriction analysis identified a clone having the prothrombin coding region inserted in the opposite orientation relative to the promoter and was designated prothrombin 4/229R backwards.

Example 2

Construction of the Tissue Plasminogen Activator Prepro Sequence

The tissue plasminogen activator (tPA) prepro sequence was isolated from Zem169, which was constructed as follows. A cDNA clone comprising the coding sequence for mature tPA was constructed from mRNA from the Bowes melanoma cell line (Rijken and Collen, *J. Biol. Chem.* 256 7035–7041, 1981). This cDNA was then used to construct the plasmid pDR1296. *E. coli* strain JM83 transformed with pDR1296 has been deposited with American Type Culture Collection under accession number 53347.

A DNA construct comprising the MT-1 promoter, complete tPA coding sequence, including the natural tPA prepro sequence, and the human growth hormone (hGH) terminator was assembled as follows. The natural tPA prepro sequence was constructed from synthesized oligonucleotides and was inserted into Bam HI-digested pUCS. A Kpn I-Bam HI fragment comprising the MT-1 promoter was isolated from MThGH112 (Palmiter et al., *Science* 22: 809–814, 1983) and inserted into pUC18 to construct Zem93. Plasmid EV142, comprising MT-1 and hGH sequences in the pBR322 derivative pBX322 (Palmiter et al., ibid.), was digested with Eco RI, and the fragment comprising the MT-1 promoter and hGH terminator sequences was isolated. This fragment was cloned into Eco RI-digested pUC13 to construct plasmid Zem4. Zem93 was then linearized by digestion with Bam HI and Sal I. Zem4 was digested Bgl II and Sal I and the hGH terminator was purified. The tPA prepro sequence was removed from the pUC8 vector as a Sau 3A fragment. The three DNA fragments were then joined, and a plasmid having the tPA prepro sequence in the correct orientation was designated Zem97. Zem97 was cut with Bgl II and the Bgl II-Bam HI tPA fragment from pDR1296 was inserted. The resultant vector was designated Zem99 (FIG. 2).

Figure 2:
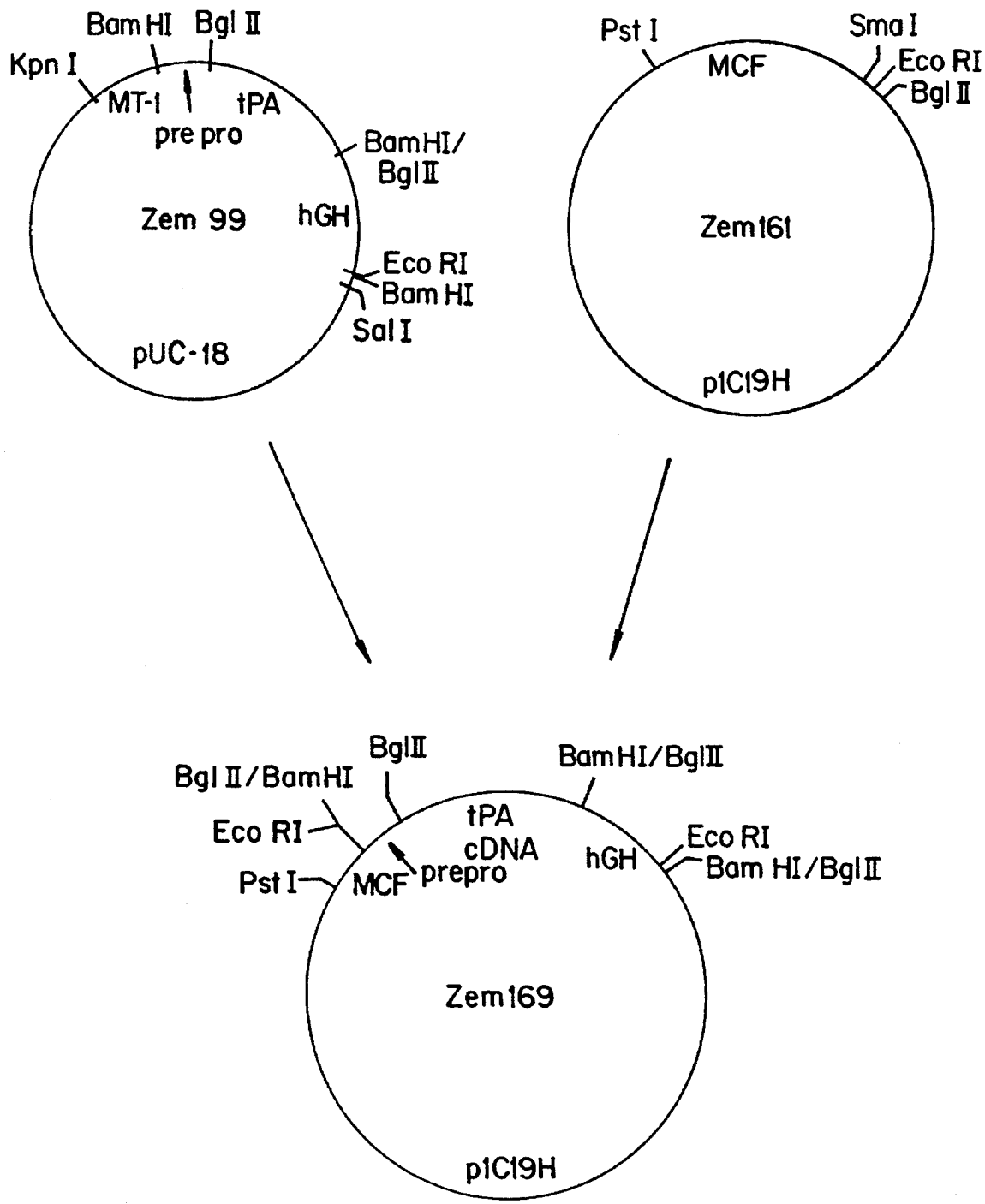
FIG. 2 illustrates the construction of plasmid Zem169. Symbols used are prepro, the tPA prepro sequence; hGH, the hGH terminator; MCF, the MCF-13 promoter.

As shown in FIG. 2, the tPA coding sequence from Zem99 was then operatively linked to the MCF-13 promoter (Yoshimura et al., *Mol. Cell. Biol.* 5: 2832–2835, (1985)). The MCF-13 promoter was obtained as a Pst I and Sma I fragment that was ligated with Pst I-Sma I linearized pIC19H. The resulting plasmid, designated Zem161, was linearized with Bgl II. The tPA coding sequence and human growth hormone terminator were isolated from Zem99 as a Bam HI fragment. The Bgl II linearized Zem161 and Bam HI tPA-hGH fragment were ligated together. A plasmid containing the insert in the correct orientation relative to the promoter was designated Zem169 (FIG. 2). The tPA leader sequence was isolated from Zem169 by digestion with Eco RI and Bgl II to isolate the 120 bp fragment.

The tPA leader was then joined with a sequence encoding protein C. Synthetic oligonucleotides ZC1237 and ZC1238 (Sequence ID Nos. 4 and 5) were designed to provide, when annealed, an adapter encoding the first eight amino acids of protein C and having a 5' Bgl II adhesive end and a 3' Sst I adhesive end. Oligonucleotides ZC1237 and ZC1238 (Sequence ID Nos. 4 and 5) were kinased essentially as described by Sambrook et al. (ibid.). The 3' protein C coding sequence was obtained from plasmid pDX/PC962 (which is described in copending commonly assigned U.S. patent application Ser. No. 07/582,131 and PCT publication WO 91/09953, which are incorporated herein by reference in their entirety), which contains the SV40 ori and enhancer, the adenovirus major late promoter and 5' and 3' splice sites, a protein C cDNA sequence and the SV40 polyadenylation signal. Plasmid pDX/PC962 was digested with Eco RI to completion and partially digested with Sst I to isolate the 1.5 kb fragment containing the 3' protein C sequence. The 120 bp Eco RI-Bgl II tPA leader fragment, ZC1237 (Sequence ID No. 4), ZC1238 (Sequence ID No. 5) and the 1.5 kb Sst I-Eco RI fragment were joined with pDX (described in U.S. Pat. No. 4,959,318 which is incorporated herein by reference), which had been linearized by digestion with Eco RI. The ligation mixture was transformed into *E. coli* strain HB101, and plasmid DNA was prepared from selected transformants. Restriction analysis of the selected plasmids showed that one plasmid, termed tPA/pC/pDX, contained the fragments in the correct order and in the correct orientation.

Example 3

Construction of Gla-domainless Prothrombin Expression Units and Expression in Mammalian Cells A. Construction of Thr100

Plasmid Thr100 was used to express a gla-domainless prothrombin which contained the A chain, the activation site and the serine protease domain of prothrombin.

A 60 base pair fragment of the tPA leader sequence was isolated from the plasmid tPA/PC/pDX (Example 2) by digestion with Eco RI and Nar I. Adapters were constructed using synthetic oligonucleotides (ZC3830, ZC3831, ZC3832, and ZC3833 (Sequence ID Nos. 12, 13, 14 and 15, respectively)) that provided the remaining 60 base pairs of the tPA leader sequence joined to a DNA segment encoding Arginine 415 through Glycine 431 of human prothrombin (Sequence ID No. 3). This adapter sequence was designed with a 5' Nar I adhesive end and a 3' Ava I adhesive end. All four oligonucleotides were kinased independently and after inactivation of the kinase were combined and annealed. A 1035 base pair Ava I to Eco RI prothrombin fragment was isolated from plasmid prothrombin 4/229R backwards (Example 1).

The 60 base pair Eco RI to Nar I tPA leader fragment, the Nar I to Ava I adapter, the Ava I to Eco RI prothrombin fragment and Eco RI-linearized Zem229R vector were ligated. The ligation mixture was used to transform *E. coli* strain HB101. Plasmid DNA was prepared from eight transformants. Restriction analysis using Nar I and Eco RI showed that one transformant contained an insert of the correct size but in a reversed orientation relative to the promoter. Plasmid DNA from that clone, designated #8, was digested with Eco RI to liberate the entire insert and the digested DNA was religated to obtain a clone having the insert in the proper orientation. From this ligation a single clone was shown to have the insert in the correct orientation. This clone, designated #15, was further analyzed using Eco RI, Pst I, Ava I, Nar I and Sac I enzymes and was found to contain all the DNA fragments in the correct sizes and orientation relative to the promoter.

Plasmid DNA from clone #15 was used in a calcium phosphate-mediated transfection (Wigler et al. ibid.) of BHK570 cells (deposited with the American Type Culture Collection, Rockville, Md., under Accession No. 10314). The transfection mixture contained between 2–10 μg of plasmid DNA and 100 μM chloroquine. The mixture was added to a 70% confluent 10 cm petri dish containing growth medium (Table 1) and incubated at 37° C. and 5% $CO_2$. After four hours the medium was removed, and the cells were glycerol shocked for one minute by the addition of DMEM (Gibco-BRL, Gaithersburg, Md.) containing 15% glycerol. After the incubation, the glycerol medium was replaced with growth medium (Table 1).

TABLE 1

| 1. Growth Medium | |
|---|---|
| 500 ml | Dulbecco's Modified Eagle's Medium (DMEM) (Gibco-BRL, Gaithersburg, MD) |
| 5% | fetal calf serum (Hyclone, Logan, UT) |
| 1 mM | sodium pyruvate (Irvine, Santa Ana, CA) |
| 0.29 mg/ml | L-glutamine (Hazelton, Lenexa, KS) |
| 2. Selection Medium | |
| 500 ml | Dulbecco's Modified Eagle's Medium (DMEM) |
| 5% | fetal calf serum |
| 1 mM | sodium pyruvate |
| 0.29 mg/ml | L-glutamine |
| 1 μM or 10 μM | methotrexate |
| 3. Serum-free Medium | |
| 500 ml | Dulbecco's Modified Eagle's Medium (DMEM) |
| 1 mM | sodium pyruvate |
| 0.29 mg/ml | L-glutamine |
| 10 mg/l | transferrin (JRH, Lenexa, KS) |
| 5 mg/l | fetuin (Aldrich, Milwaukee, WI) |
| 5 mg/l | insulin (Gibco, Grand Island, NY) |
| 2 μg/l | selenium (Aldrich, Milwaukee, WI) |

Twenty-four hours after transfection the cells were trypsinized, and either 10% or 2.5% of the cells were replated in selection medium (Table 1). The cells were grown until colonies were well established. Independent colonies were picked into 24-well plates (American Scientific Products, Chicago, Ill.) and were grown until confluent. When the cells were confluent the medium from each well was replaced with 0.5 ml serum-free medium (Table 1).

After twenty-four hours in the serum-free medium, the media were collected and tested for reactivity in a chromogenic assay (Example 4). No reactivity was demonstrated, and subsequent sequence analysis of the DNA from clone #15 revealed two mutations. The sequence spanning oligonucleotide ZC3833 (Sequence ID No. 15) contained a substitution at base 42 from T to A, resulting in a Tyr to Phe substitution. This substitution is a conservative substitution, and it was determined that the sequence did not need to be corrected. In addition, the sequence spanning oligonucleotide ZC3831 (Sequence ID No. 13) was found to have a deletion at base 29 that caused a frameshift.

To correct the deletion, plasmid DNA from clone #15 was digested with Eco RI and BssH I to isolate the approximately 119 bp fragment encoding the tPA leader and ZC3833:ZC3830 (Sequence ID Nos. 15 and 12, respectively) adapter sequences. Plasmid DNA from clone #15 was also digested with Ava I and Eco RI to isolate the approximately 1 kb fragment containing the prothrombin cDNA sequence. The mutations in oligonucleotides ZC3831 and ZC3832 (Sequence ID Nos. 13 and 14) were the result of minor contaminations of the oligonucleotide preparations and as such new oligonucleotides were not synthesized. Oligonucleotides ZC3831 and ZC3832 (Sequence ID Nos. 13 and 14) were kinased and annealed. The 119 bp Eco RI-BssH I fragment, the kinased and annealed ZC3831:ZC3832 adapter (Sequence ID Nos. 13 and 14), the 1 kb Ava I-Eco RI prothrombin fragment, and Eco RI-linearized Zem229R were ligated. The ligation mixture was used to transform *E. coli* strain XL-1 cells. After restriction and sequence analysis of plasmid DNA from selected transformants, several clones were found to contain the correct sequence spanning ZC3831 (Sequence ID No. 13). A clone containing the correct sequence at ZC3831 (Sequence ID No. 13) and comprising the mouse metallothionen promoter; the tPA leader; the A chain and the serine protease domain of human prothrombin; and the SV40 polyadenylation signal was designated Thr100.

Alternatively, both mutations may be repaired by religating all the parts of the construction as initially described and screening the resulting plasmids by sequence analysis. Resynthesis of the oligonucleotides was not required because, as stated previously, the errors were minor contaminants in the oligonucleotide preparations.

Plasmid Thr100 was used transfect BHK570 cells as described above. The transfectants were grown and media from transfected cells were assayed as described above. The chromogenic assay (Example 4) showed that Thr100 clone 1 expressed gla-domainless prothrombin at 9.4 μg/ml and Thr100 clone 3 expressed gla-domainless prothrombin at 3.4 μg/ml.

B. Construction of Thr101

The plasmid Thr101 was used to express a gla-domainless prothrombin, which contained kringle 2, the A-chain, the wild-type thrombin activation site and the serine protease domain of human prothrombin.

The full 120 base pair tPA leader was isolated from tPA/PC/pDX. This fragment was isolated as an Eco RI-Bgl II fragment. Synthetic oligonucleotides ZC3858 and ZC3859 (Sequence ID Nos. 16 and 17) were designed to provide an 80 base pair adapter after annealing. The adapter encodes a human prothrombin sequence from Serine 192 through Arginine 217 and contains a 5' Bgl II adhesive end and a 3' Hae II adhesive end. The C-terminal prothrombin sequence was obtained from plasmid prothrombin 4/229R backwards (Example 1) as a Hae II to Eco RI fragment.

The Eco RI to Bgl II tPA leader sequence, the Bgl II to Hae II adapter, the Hae II to Eco RI prothrombin cDNA fragment, and Eco RI-linearized Zem229R were ligated. The ligation mixture was used to transform E. coli strain HB101, and plasmid DNA from selected transformants was analyzed using Nar I, Eco RI, Pst I, Ava I, Sst I, and Xho I. This analysis revealed a clone having an insert of the expected size but in reverse orientation relative to the promoter. The plasmid DNA from this clone, designated #1, was digested with Eco RI, to liberate the insert from the vector, and was religated. Plasmid DNA from selected transformants was analyzed by restriction analysis to identify a clone having an insert in the proper orientation relative to the promoter.

A single clone having the insert in the correct orientation, designated #21 and subsequently re-named Thr100, was used in a calcium phosphate-mediated transfection of BHK570 cells as described previously. The transfected cells were grown, and independent colonies were picked and plated into 24-well plates as described above. The media was changed to serum-free media once the cells were confluent. After 24 hours chromogenic activity was determined using a chromogenic assay (Example 4). Clone #29 was found to express gla-domainless prothrombin at 20 µg/ml.

C. Construction of Thr102

Plasmid Thr102 was used to express a gla-domainless prothrombin that contained kringle 1, kringle 2, the A chain, the wild-type thrombin activation site and the serine protease domain of human prothrombin.

The entire 120 base pair tPA leader was isolated as an Eco RI-Bgl II fragment from plasmid tPA/PC/pDX (Example 2). Synthetic oligonucleotides ZC3860 and ZC3861 (Sequence ID Nos. 18 and 19) were designed to form, when annealed, an adapter comprising a DNA segment encoding from Serine 68 to Proline 89 of human prothrombin and providing a 5' Bgl II adhesive end and a 3' Xho I adhesive end. A prothrombin cDNA encoding kringle 1, kringle 2, the A chain, the wild-type thrombin activation site and the serine protease domain was isolated from plasmid prothrombin 4/229R backwards as an Xho I-Eco RI fragment.

The Eco RI to Bgl II tPA leader sequence, the Bgl II to Xho I adapter, the Xho I to Eco RI prothrombin cDNA fragment, and Eco RI-linearized vector Zem229R were ligated. The ligation mixture was used to transform E. coli strain HB101, and plasmid DNA from selected transformants was analyzed using Nar I, Eco RI, Pst I, Ava I, Sst I, Xba I, BssH I and Xho I as described previously. A single clone, designated Thr102, was found to have an insert of the correct size and in the correct orientation relative to the promoter. Plasmid DNA prepared from this clone was used in a calcium phosphate-mediated transfection of BHK570 cells as described above. Independent colonies were picked into 24-well plates and were amplified in selection medium containing 10 µM methotrexate. Once the cells were confluent, gla-domainless prothrombin was measured using a chromogenic assay (Example 4). A clone, designated #15, was shown to express gla-domainless prothrombin at 9.9 µg/ml.

D. Construction of the KEX2 Expression Vector KEX2/Zem228

The Saccharomyces cerevisiae KEX2 gene was isolated from a yeast genomic library by screening transformed kex2 mutant cells for production of an α-factor halo on a lawn of suitable tester cells. One clone was obtained that complemented all reported defects of kex2 mutants (mating, afactor production, maturation of killer toxin and sporulation in a homozygous diploid strain). The gene was subcloned into a pUC vector under the control of the yeast GAL1 promoter. The resultant plasmid, designated p1515, has been deposited with American Type Culture Collection, 12301 Parklawn Dr., Rockville, Md. 20221, under accession number 67569. Plasmid p1515 was digested with Hind III, and a 2.1 kb fragment was recovered. This fragment was ligated to Hind III-cut pUC18 to construct plasmid pUC18/KEX2. The KEX2 fragment (2.1 kb) was then isolated from pUC18/KEX2 by digesting the plasmid partially with Hind III and to completion with Bam HI. The remainder of the KEX2 sequence was then isolated as a 0.43 kb fragment from a Bam HI + Hind III digest of p1515.

The two KEX2 fragments were then ligated into the Bam HI site of the vector Zem228. Zem228 is a pUC18-based expression vector containing a unique Bam HI site for insertion of foreign DNA between the mouse metallothionein-I promoter and SV40 transcription terminator. Zem228 also contains an expression unit comprising the SV40 early promoter, a neomycin resistance gene, and SV40 terminator. The resulting plasmid was designated KEX2/Zem228.

E. Construction of Plasmids Containing Alternative Cleavage Sites in Place of the Wild-Type Thrombin Activation Site The wild-type thrombin activation site (Arg-Ile) was replaced with an activation site comprising the amino acid sequence RRKR (Sequence ID No. 34) by adapter insertion of the alternative cleavage site between the A chain and serine protease domains of the prothrombin coding region of Thr100. Oligonucleotides ZC3932, ZC3933, ZC3934 and ZC3936 (Sequence ID Nos. 22, 23, 24 and 25, respectively) were designed to provide, when annealed, a Sac I-Mro I adapter encoding a RRKR (Sequence ID No. 34) activation site and flanking A-chain and serine protease domain sequences. Oligonucleotides ZC3932 and ZC3934 (Sequence ID Nos. 22 and 24, respectively) were each kinased. Oligonucleotide pairs ZC3933 and ZC3932 (Sequence ID Nos. 23 and 22, respectively) and ZC3936 and ZC3934 (Sequence ID Nos. 25 and 24, respectively) were annealed. Plasmid Thr100 was digested with Eco RI and Sac I to isolate the 0.243 kb fragment comprising the 5' coding sequence of the A chain, and with Mro I and Eco RI to isolate the 0.88 kb fragment comprising the 3' coding sequence of the serine protease domain. The oligonucleotide pairs were ligated with the 0.243 kb Eco RI-Sac I fragment, the 0.88 kb Mro I-Eco RI fragment and Zem229R, which had been linearized by digestion with Eco RI and treated with calf alkaline phosphatase to prevent recircularization. The resulting ligation mixture was used to transform E. coli strain XL-1 cells. Plasmid DNA prepared from selected transformants was screened by restriction analysis, and a plasmid containing the gladomainless prothrombin coding region in the correct orientation with respect to the promoter was designated Thr103.

A DNA construct encoding Kringle 2, the A chain, an inserted RRKR activation site (Sequence ID No. 34) and the serine protease domain was constructed from plasmid Thr103. A 0.591 kb Eco RI-Sac I fragment comprising the Kringle 2 5' A chain coding sequences of human prothrombin was obtained from plasmid Thr101. Plasmid Thr103 was digested with Sac I and Eco RI to isolate the 0.97 kb fragment comprising the 3' coding sequence of the A chain of human prothrombin, the inserted RRKR activation site (Sequence ID No. 34), and the serine protease domain coding sequence. The 0.591 kb Eco RI-Sac I fragment was ligated with the 0.970 kb Sac I-Eco RI fragment and Zem229R that had been linearized with Eco RI and treated with calf alkaline phosphatase to prevent recircularization. The resulting ligation mixture was used to transform *E. coli* strain XL-1 cells. Plasmid DNA prepared from selected transformants was screened by restriction analysis, and a plasmid containing the gla-domainless prothrombin coding region in the correct orientation with respect to the promoter was designated Thr122.

An analogous plasmid construct comprising a DNA segment encoding the Kringle 2 of human prothrombin, the A chain of human prothrombin, an LDKR KEX2 cleavage site replacing the wild-type thrombin cleavage site (Sequence ID No. 35) and the serine protease domain of human prothrombin was made using the same restriction digestions to obtain fragments comprising the Kringle 2 coding sequence and the 5' coding sequence of the A chain; the 3' coding sequence of the serine protease domain; and vector sequences. These fragments were joined with an adapter that provided the 3' coding sequence of the A chain, the LDKR cleavage site coding sequence (Sequence ID No. 35) and the 5' coding sequence of the serine protease domain to form plasmid Thr127.

Plasmid Thr122 and KEX2/Zem228 were co-transfected into the mammalian cell line BHK 570 (deposited with the American Type Culture Collection under accession number 10314) using the Boehringer Mannheim transfection-reagent N-[1-(2,3-Dioleoyloxy)propyl]-N,N,N-trimethyl ammoniummethylsulfate (Boehringer Mannheim, Indianapolis, Ind.) using the manufacturer-supplied directions. The transfectants were grown, and media from transfected cells were assayed in the chromogenic assay (Example 4). The results of the chromogenic assay showed that the clones produced approximately 300 ng/l of thrombin.

The wild-type thrombin activation site and two amino acid codons immediately upstream from the activation site were replaced with a DNA segment encoding RRKR (Sequence ID No. 34) to construct a plasmid containing a DNA segment encoding the A-chain of human prothrombin, an RRKR (Sequence ID No. 34) cleavage site and the serine protease domain of human prothrombin. Oligonucleotides ZC4713, ZC4720, ZC4721, and ZC4722 (Sequence ID Nos. 26, 27, 28 and 29, respectively) were designed to provide, when annealed, a Sac I-Mro I adapter encoding the RRKR cleavage site (Sequence ID No. 34) coding sequence flanked by 3' A-chain and 5' serine protease domain coding sequences. Oligonucleotides ZC4720 (Sequence ID Number 27) and ZC4721 (Sequence ID Number 28) were each kinased, and each oligonucleotide was annealed with its companion oligonucleotide (ZC4713:ZC4720 (Sequence ID Nos. 26 and 27, respectively) and ZC4721::ZC4722 (Sequence ID Nos. 28 and 29, respectively)). Plasmid Thr100 was digested with Eco RI and Sac I to isolate the 0.243 kb fragment encoding the 5' coding sequence of the A chain and with Mro I and Eco RI to isolate the 0.88 kb fragment encoding the 3' coding sequence of the serine protease domain. The oligonucleotide pairs were ligated with the 0.243 kb Eco RI-Sac I fragment, the 0.88 kb Mro I-Eco RI fragment and Zem229R, which had been linearized by digestion with Eco RI and treated with calf alkaline phosphatase to prevent recircularization. The resulting ligation mixture was used to transform *E. coli* strain XL-1 cells. Plasmid DNA prepared from selected transformants was screened by restriction analysis, and a plasmid containing the gla-domainless prothrombin coding region in the correct orientation with respect to the promoter was designated Thr115.

A DNA construct encoding the Kringle 2 and A chain of human prothrombin, a RRKR activation site (Sequence ID No. 34) replacing the wild-type thrombin activation site and two amino acid codons immediately upstream and the serine protease domain of human prothrombin was constructed from plasmid Thr115. A 0.591 kb Eco RI-Sac I fragment encoding Kringle 2 and 5' A chain coding sequence of human prothrombin was obtained from plasmid Thr101. Plasmid Thr115 was digested with Sac I and Eco RI to isolate the 0.97 kb fragment comprising the 3' A chain coding sequence, the altered activation site, and the serine protease domains coding sequence. The 0.591 kb Eco RI-Sac I fragment was ligated with the 0.970 kb Sac I-Eco RI fragment and Zem229R that had been linearized with Eco RI and treated with calf alkaline phosphatase to prevent recircularization. The resulting ligation mixture was used to transform *E. coli* strain XL-1 cells. Plasmid DNA prepared from selected transformants was screened by restriction analysis, and a plasmid containing the gla-domainless prothrombin coding region in the correct orientation with respect to the promoter was designated Thr121.

An analogous plasmid constructs comprising a DNA segment encoding the Kringle 2 and A chain of human prothrombin, an LDKR (Sequence ID No. 35) KEX2 cleavage site that replaced the wild-type thrombin activation site and the two amino acid codons immediately upstream of the wild-type thrombin activation site and the serine protease domain of human prothrombin was made using the same restriction sites to obtain fragments comprising the Kringle 2 and 5' A chain coding sequences; the 3' coding sequence of the serine protease domain; and vector sequences. These fragments were joined with an adapter that provided a DNA segment comprising the 3' A chain coding sequence, the LDKR cleavage site coding region and serine protease domain coding sequence to form Thr128.

Plasmid Thr121 and KEX2/Zem228 were co-transfected into the mammalian cell line BHK 570 (deposited with ATCC under accession number 10314) using the Boehringer Mannheim Transfection-Reagent. The transfectants were grown, and media from transfected cells were assayed in the chromogenic assay (Example 4). The results of the chromogenic assay showed that the clones produced approximately 300 ng/l of thrombin.

F. Construction of Plasmid Thr118

The wild-type thrombin activation site (Arg-Ile) present in plasmid Thr100 was replaced with a thrombin cleavage site by adapter insertion. Oligonucleotides ZC4738, ZC4781, ZC4741, and ZC4742 (Sequence ID Nos. 30, 33, 31 and 32, respectively) were designed to provide, when annealed, a Sac I-Mro I adapter containing a DNA segment encoding the carboxyl-terminal portion of the A-chain, a thrombin cleavage site and the amino terminal portion of the serine protease domain. Oligonucleotides ZC4781 and ZC4741 (Sequence ID Nos. 33 and 31, respectively) were each kinased and were annealed with the appropriate partner oligonucleotide (ZC4781::ZC4738 (Sequence ID Nos. 33 and 30, respectively) and ZC4741::ZC4742 (Sequence ID Nos. 31 and 32, respectively)). Plasmid Thr100 was digested with Eco RI and Sac I to isolate the 0.243 kb fragment containing the 5' coding sequence of the A chain of human prothrombin and with Mro I and Eco RI to isolate the 0.88 kb fragment containing the 3' coding sequence of the serine protease domain of prothrombin. The annealed oligonucleotide pairs ZC4781::ZC4738 (Sequence ID Nos. 33 and 30, respectively) and ZC4741::ZC4742 (Sequence ID Nos. 31 and 32, respectively) were ligated with the 0.243 kb Eco RI-Sac I Thr100 fragment, the Mro I-Eco RI Thr100 fragment and Zem229R that had been linearized with Eco RI and treated with calf alkaline phosphatase to prevent recircularization. A 3 µl aliquot of the ligation mixture was transformed into *E. coli* strain XL-1 cells. Plasmid DNA prepared from selected transformants was screened by restriction analysis. A plasmid containing a DNA sequence encoding the A-chain of human prothrombin, a thrombin cleavage site and the serine protease domain of human prothrombin in the correct orientation relative to the promoter was termed Thr118.

Plasmid Thr118 was transfected into BHK 570 cells using the Boehringer Mannheim Transfection-Reagent as described above. The transfectants were grown, and media from transfected cells were assayed in the chromogenic assay (Example 4). A clone of transfected cells was selected, grown and seeded into each well of two 6-well plates. The growth media (Table 1) from each well was replaced with serum-free medium (Table 1) containing additives as shown in Table 2.

TABLE 2

| Well # | Additive | Thrombin (µg/ml) |
|---|---|---|
| 1 | none | 0.14 |
| 2 | none | 0.18 |
| 3 | none | 0.18 |
| 4 | 0.1 U/ml heparin (Sigma) | 0.18 |
| 5 | 1 U/ml heparin | 1.1 |
| 6 | 10 U/ml heparin | 0.56 |
| 7 | 10 ng/ml snake venom activator | 0.15 |
| 8 | 50 ng/ml snake venom activator | 0.45 |
| 9 | 200 ng/ml snake venom activator | 1.0 |
| 10 | 10 ng/ml thrombin (Dr. Walt Kisiel University of New Mexico, Albuquerque, NM) | 0.18 |
| 11 | 100 ng/ml thrombin | 0.23 |
| 12 | 1000 ng/ml thrombin | 1.1 |

The plates were incubated for 24 hours at 37° C., following which the medium from each well was assayed using the chromogenic assay described in Example 4 except that the step of activation with snake venom activator was omitted. The results of the assay are shown in Table 2 and indicate that the gla-domainless prothrombin produced from Thr118 is capable of self-activation in the presence of low levels of heparin, snake-venom activator or thrombin.

To test the auto-activation of the gla-domainless prothrombin produced from Thr118-transfected cells, a randomly selected Thr118-transfected clone was split into a six-well plate and grown to confluency in serum-free medium. To each well, 2 µg/ml of thrombin was added in 2 ml of serum-free medium, and the plates were incubated. After two days, 90% of the medium was removed and replaced with fresh serum-free medium without thrombin, and the plates were incubated. After three days incubation, 90% of the medium was removed from each well and replaced with fresh serum-free medium without thrombin. A sample of the spent medium from each well was assayed in the chromogenic assay. The results showed that the cells made approximately 2.5 µg/ml of thrombin. The plates were incubated for three days, after which 90% of the medium was replaced as before, and an aliquot of the spent medium was assayed as above. The results of the assay showed that the cells produced approximately 2 µg/ml of thrombin. The plates were incubated four days and the media was changed and assayed as described above. The results of the assay showed that the cells produced approximately 1 µg/ml of thrombin.

Example 4

Purification of Thrombin Precursors and Activity Assays

A. Purification of Thrombin from Transfected Host Cells

Thrombin precursors were purified from selected transfectants that were grown under selection to confluency in 150 mm tissue culture plates. Once the transfectants reached confluency, the spent medium from each plate was removed, discarded and replaced with 25 ml of serum-free medium (Table 2). Two or three times per week, the spent media were collected and stored at −20° C., and 25 ml of fresh serum-free medium was added to each plate. The stored media for each transfectant were thawed, pooled and filtered through a 0.45 µm filter (Nalge, Rochester, N.Y.). Sodium azide was added to the filtered media to a final concentration of 0.2% (v/v).

Filtered media from Thr102 transfectants were applied to an AFFI-GEL® BLUE column (Bio-Rad, Richmond, Calif.). The thrombin precursors were eluted from the column with 1M NaCl, 25 mM Tris pH 7.4. The A280 peak was collected. If the volume of the collected peak is too great, the sample may be concentrated using a Centricon concentrator (Amicon, Arlington Heights, Ill.). The pooled fractions were diluted 2-fold with 25 mM Tris, pH 7.4.

Purified *Echis carinatus* venom activator was obtained from Dr. Walt Kisiel (University of Mexico, Albuquerque, N.M.). Briefly, the venom activator was purified from crude venom by sequential gel filtration on Sephadex G-150, DEAE-Sephadex A25 columns followed by repetitive MONO Q FPLC. By SDS-polyacrylamide gel electrophoresis in both the presence and absence of mercaptoethanol, the venom activator migrated as a single band with an apparent Mr of 80,000. The purified activator was dissolved in 0.5 M Tris-HCl, pH 8.0 containing approximately 0.2 M NaCl.

The thrombin precursors present in the pooled $A_{280}$ peak were activated by the addition of a dilution of between 1:1,000 and 1:2,000 (w/w) snake venom activator based on an estimated protein concentration. The mixture was incubated for four hours at 37° C. to allow for complete activation of the peak protein. After the incubation, the material was applied to a Benzamidine Sepharose 4B column (Pharmacia LKB Biotechnology Inc., Piscataway, N.J.). The column was washed with 1 M NaCl, 25 mM Tris, pH 7.4 and was eluted with 15 mM Benzamidine in TBS. Fractions were collected, and aliquots of each sample were diluted 200 to 500-fold in TBS, 1 mg/ml BSA. A twenty to fifty microliter aliquot of each diluted sample was assayed by chromogenic assay to identify the fractions containing thrombin activity.

Human plasma prothrombin (obtained from Dr. Walt Kisiel, University of New Mexico; human prothrombin may be purchased from Sigma, St. Louis, Mo.) was used as a standard in the chromogenic assay. Twenty micrograms of human plasma prothrombin was serially diluted in TBS, pH 7.4 (Sambrook et al., ibid.) + 1 mg/ml bovine serum albumin to concentrations of 20 µg/ml, 10 µg/ml, 5 µg/ml, 2.5 µg/ml, 1.25 µg/ml, 0.625 µg/ml, 0.312 µg/ml, and 0.156 µg/ml. Duplicate 10 µl standards were added to wells of a 96-well microtiter plate.

Twenty to fifty microliters of each sample and 10 µl of each standard were added to the wells of a 96-well microtiter plate. Each sample and standard received 40 µl of 1 mM thrombin chromogenic substrate (American Diagnostica, New York, N.Y.). Buffer (TBS, 1 mg/ml BSA) was added to each sample and standard to bring the final assay volume to 100 μl. The plates were incubated for approximately five minutes at room temperature to allow for color development. Absorbance at 405 nm was read for each standard and sample. The fractions showing peak thrombin activity were pooled. The pooled fractions may be desalted by applying the material to a G-25 column (Bio-Rad).

B. Chromogenic Assay

Chromogenic assays to determine thrombin activity levels were carried out by adding 10 μl of appropriately diluted sample (in TBS, pH 7.4, 1 mg/ml BSA) or standard (described above) to wells of a 96-well microtiter plate. To each sample, 80 μl of 0.5 μg/ml of snake venom activator diluted in TBS, pH 7.4+1 mg/ml bovine serum albumin was added. The samples were incubated at 37° C. for one hour. After incubation, 50 μl of 0.5 mM thrombin chromogenic substrate (American Diagnostica, New York, N.Y.) was added, and the plates were allowed to incubate for approximately 5 min. at room temp. to allow for color development. Absorbance at 405 nm was read for each standard and sample. The sample absorbance values were averaged and compared to the standard curve to determine the amount of activatable thrombin precursor present.

The peak sample was diluted eight-fold with water and $E.$ $carinatus$ activator was added to a wt:wt ratio of activator:activatable thrombin precursor from 1:100 to 1:1000. The sample was then incubated from 1 to 4 hr. at 37° C. Aliquots of the activated sample were electrophoresed in reducing and non-reducing acrylamide gels to confirm conversion of the precursor to thrombin.

Example 5

Construction of Gla-Domainless Prothrombin Expression Units and Expression in Yeast Cells A. Construction of pZH10

A DNA construct comprising a DNA molecule encoding a thrombin precursor comprising Kringle 2, A chain and serine protease domains of human prothrombin was constructed. Plasmid prothrombin, comprising the prothrombin coding sequence subcloned as a Pst I fragment in plasmid pBR322, was digested with Nar I and Bcl I to isolate the 1.2 kb fragment encoding the Kringle 2 coding sequence, the A chain coding sequence and the 5' coding sequence of the serine protease domain of human prothrombin.

The TPI1 promoter, MFα1 signal sequence and TPI1 terminator sequences were obtained from a prethrombin expression unit constructed by first preparing a synthetic Hind III-Sst I adapter comprising a yeast codon-optimized sequence encoding amino acids Ser-Leu-Asp, corresponding to amino acids 81–83 of the alpha factor prepro sequence, a Lys-Arg KEX2 cleavage site and the amino terminal amino acid sequence of prethrombin (amino acids 308 through 345 of Sequence ID Number 1). Oligonucleotides ZC1562, ZC1563, ZC1564 and ZC1565 (Sequence ID Nos. 39, 40, 41 and 42, respectively) were kinased and annealed to form the Hind III-Sst I adapter described above. A second oligonucleotide adapter was synthesized to provide, when annealed, a Bcl I-Xba I adapter comprising a yeast codon-optimized sequence encoding the carboxyl-terminal amino acids of prethrombin (amino acids 611 to 615 of Sequence ID Number 1) followed by a stop codon. Synthetic oligonucleotides ZC1629 and ZC1630 (Sequence ID Nos. 43 and 44; respectively) were kinased and annealed to form the Bcl I-Xba I adapter. Plasmid prothrombin was digested with Sst I and Bcl I to isolate the 787 base pair prothrombin fragment. The Hind III-Sst I adapter, the Sst I-Bcl I prothrombin fragment and the Bcl I-Xba I adapter were joined with Hind III-Xba I-linearized pUC19 in a four-way ligation. The resulting plasmid, designated pTHR1, comprises a DNA segment encoding the amino-terminal amino acid sequence of the MFα1 signal, a KEX2 cleavage site and a human prethrombin.

The TPI1 promoter and alpha factor signal sequence were obtained from plasmid pTGFαCB. The plasmid pTGFαCB was derived from plasmid pB12, which comprises the TPI1 promoter, the MFα1 signal sequence, PDGF-BB sequence, the TPI1 terminator and pIC19R vector sequences. The construction of pB12 is disclosed in U.S. Pat. No. 4,766,073, incorporated herein by reference. The MFα1 signal sequence and PDGF-BB sequence from pB12 were subcloned as an Eco RI-Xba I fragment into M13. The Sst I site present in the MFα1 signal sequence was changed to a Hind III site by in vitro mutagenesis using the method described by Kunkel et al. (U.S. Pat. No. 4,873,192, incorporated herein by reference) and oligonucleotide ZC1159 (Sequence ID No. 36). A clone having a Hind III site in place of the Sst I site was identified. A fragment containing the MFα1 signal sequence was isolated as an Eco RI-Hind III fragment. The Eco RI-Hind III fragment containing the MFα1 signal sequence and a Hind III-Xba I fragment containing a synthesized transforming growth factor α (TGFα) coding sequence were ligated with Eco RI-Xba I linearized pUC13. The resultant plasmid, designated αfTGFα/pUC13, was digested with Eco RI and Xba I to isolate the MFα1-TGFα insert, which was cloned into p170CB/pBR. The construction of plasmid p170CB/pBR is described by Murray (copending U.S. patent application Ser. No. 07/557,219, and WO 92/01716, which are incorporated herein by reference), and it contains the TPI1 promoter, MFα1 signal sequence, PDGF-BB coding sequence, the TPI1 terminator and pBR322 vector sequences. Plasmid pB170CB/pBR was digested with Eco RI-Xba I to isolate the fragment containing the TPI1 promoter, pBR322 vector sequence and the TPI1 terminator. The Eco RI-Xba I pB170CB/pBR fragment and the Eco RI-Xba I MFα1-TGFα fragment were ligated. The resulting plasmid, designated TGFαCB, comprises the TPI1 promoter, the MFα1 signal sequence, a TGFα coding sequence and TPI1 terminator.

To construct a prethrombin expression vector, plasmid TGFαCB was digested with Hind III and Xba I to isolate the fragment containing the MFα1 signal, the TPI1 promoter, pBR322 vector sequences and the TPI1 terminator. Plasmid pTHR1 was digested with Hind III and Xba I to isolate the MFα1-prethrombin coding sequence. The two fragments were ligated, and the resulting plasmid was designated pTHR2.

In the construction of a yeast expression unit capable of directing the secretion of a gla-domainless prothrombin, plasmid pTHR2 served as the source of the TPI1 promoter, MFα1 signal sequences and TPI1 terminator. Plasmid pTHR2 was digested with Hind III and Bcl I to isolate the 5.97 kb fragment comprising the TPI1 terminator, vector sequences, TPI1 promoter and MFα1 signal sequence. An adapter for joining the MFα1 prepro to the second Kringle domain via a KEX2 cleavage site was formed by the kination and annealing of oligonucleotides ZC5344 (Sequence ID No. 47) and ZC5345 (Sequence ID No. 48). The adapter comprises Hind III and Nar I adhesive ends flanking a DNA sequence encoding a KEX2 cleavage site immediately preceding amino acids Serine, amino acid 192 to 216 of prothrombin (Sequence ID No. 2). Another adapter, which contained 15 base pairs of the terminal prothrombin coding region and adhesive ends for joining the 3' end of the thrombin precursor coding sequence with the TPI1 terminator was formed by the kination and annealing of oligonucleotides ZC1630 (Sequence ID No. 44) and ZC1629 (Sequence ID No. 43). The 5.97 kb fragment from pTHR2, the ZC5344/ZC5345 adapter, the 1.2 kb fragment from prothrombin and the ZC1630/ZC1629 adapter were ligated to form plasmid pZH6. Plasmid pZH6 comprises the TPI1 promoter; MFα1 signal sequence; Kringle 2, the A chain, and the serine protease domain of human prothrombin; and the TPI1 terminator.

Plasmid pDPOT was derived from plasmid pCPOT by replacing the 750 bp Sph I-Bam HI fragment of pCPOT containing 2 micron and pBR322 sequences with a 186 bp Sph I-Bam HI fragment derived from the pBR322 tetracycline resistance gene. (Plasmid pCPOT has been deposited with ATCC as an *E. coli* strain HB101 transformant and has been assigned accession number 39685. It comprises the entire 2 micron plasmid DNA, the leu2-d gene, pBR322 sequences and the *Schizosaccharomyces pombe* POT1 gene.)

Plasmid pRPOT was derived from plasmid pDPOT by replacing the Sph I-Bam HI fragment with a polylinker. Plasmid pDPOT was digested with Sph I and Bam HI to isolate the 10.8 kb fragment. Oligonucleotides ZC1551 and ZC1552 (Sequence ID Nos. 37 and 38) were designed to form an adapter with a Bam HI adhesive end and an Sph I adhesive end flanking Sma I, Sst I and Xho I restriction sites. Oligonucleotides ZC1551 and ZC1552 (Sequence ID Nos. 37 and 38) were kinased and annealed to form the Bam HI-Sph I adapter. The 10.8 kb pDPOT fragment was circularized by ligation with the ZC1551/ZC1552 adapter. The resultant plasmid was termed pRPOT.

The expression unit present in plasmid pZH6 was subcloned into pRPOT by first digesting pZH6 with Bgl II and Hind III to isolate the 1.2 kb fragment comprising the TPI1 promoter and MFα1 prepro. Plasmid pZH6 was also digested with Hind III and Sph I to isolate the 2.2 kb fragment comprising the thrombin precursor coding sequence and TPI1 terminator. The two fragments were ligated into Bam HI-Sph I-linearized pRPOT. The resultant plasmid was designated pZH10.

B. Construction of pZH8

A DNA construct comprising a DNA molecule encoding a thrombin precursor comprising Kringle 1, Kringle 2, the A chain and the serine protease domain of human prothrombin was prepared. Plasmid prothrombin was digested with Xho I and Bcl I to isolate the 1.6 kb fragment comprising a DNA segment encoding the Kringle 1 and 2 coding sequences, the A chain coding sequence and the 5' coding sequence of the serine protease domain. Plasmid pZH6 was digested with Hind III and Bcl I to isolate the 5.99 kb fragment comprising the MFα1 signal sequence, the TPI1 promoter, vector sequences, the TPI1 terminator and the terminal 15 base pairs of the prothrombin coding sequence. An adapter for joining the MFα1 prepro to Kringle 1 was formed by the kination and annealing of oligonucleotides ZC5339 (Sequence ID No. 45) and ZC5340 (Sequence ID No. 46). The adapter comprises a 5' Hind III adhesive end that destroys the Hind III site, a DNA segment encoding a KEX2 cleavage site immediately preceding amino acids Serine, amino acid 68 to 89 of prothrombin (Sequence ID No. 2) and a 3' Xho I adhesive end. The 1.56 kb Xho I-Bcl I fragment from plasmid prothrombin, the 5.99 kb Bcl I-Hind III fragment from pZH6 and the Hind III-Xho I adapter were ligated to construct plasmid pZH5.

The expression unit present in plasmid pZH5 was subcloned into pRPOT by first digesting pZH5 with Bgl II and Xho I to isolate the 1.31 kb fragment comprising the TPI1 promoter and MFα1 prepro. Plasmid pZH5 was also digested with Xho I and Sph I to isolate the 2.45 kb fragment comprising the thrombin precursor coding sequence and TPI1 terminator. The two fragments were ligated into Bam HI-Sph I-linearized pRPOT. The resultant plasmid was designated pZHS.

C. Expression of pZH10 and pZH8 in Yeast Cells

Plasmids pZH10, comprising a DNA segment encoding the second kringle, A chain and serine protease domains of thrombin and pZH8, comprising a DNA segment encoding Kringles 1 and 2, the A chain and the serine protease domain of thrombin were transformed into *Saccharomyces cerevisiae* strains ZM114 (MATα leu2-3,112 ade2-101 ura3-52 Δpep4::TPI1prom-CAT gal2 suc2-Δ9 Δtpi1::URA3 vpt3) and ZM118 (MATα/MATα ura3/ura3 Δtpi1::URA3/Δtpi1::URA3 bar1/bar1 pep4::URA3/pep4::URA3 [cir°]) using the method essentially described by Hinnen et al. (ibid.). Transformants were selected for their ability to grow in the presence of glucose as the sole carbon source.

Selected ZM114 and ZM118 transformants were assayed for their ability to produce activatable thrombin by inoculating a 5 ml overnight YEPD culture of each transformant into 1.2 L YEPD + 6% glucose in a 2.5 L flask and incubating the cultures for 60 hrs at 30° C. in a shaker. Samples of 100 ml each were taken at 24, 36, 48 and 60 hrs post inoculation. The samples were centrifuged and the spent medium assayed for the presence of activated thrombin in a chromogenic assay.

Human plasma prothrombin standards were prepared using human plasma prothrombin obtained from Dr. Walt Kisiel (University of New Mexico). The human prothrombin was diluted in activation buffer (described below) at 5.0 μg/ml, 2.5 μg/ml, 2.0 μg/ml, 1.5 μg/ml, 1.0 μg/ml, 0.5 μg/ml, 0.4 μg/ml, and 0.3 μg/ml. Duplicate samples of standard were added to the wells of a 96-well microtiter plate.

To each 20 μl sample of supernatant, 80 μl of 1 μg/ml of snake venom activator diluted in activation buffer (20 nM Tris (pH 7.4), 150 mM NaCl, 0.2% Na azide) was added. The samples were incubated at 37° C. for one hour. After incubation, 100 μl of 0.25 mM thrombin chromogenic substrate (American Diagnostica) was added, and the plates were allowed to incubate for one to three hours to allow for color development. Absorbance at 405 nm was read for each standard and sample. The sample absorbance values were averaged and compared to the standard curve to determine the amount of activatable thrombin precursor present. Table 3 shows the results of the assay.

TABLE 3

| Strain[plasmid] | Levels of Activatable Thrombin (μg/ml) | | | |
| --- | --- | --- | --- | --- |
|  | 24 hrs | 36 hrs | 48 hrs | 60 hrs |
| ZM118[DPOT] | 0 | 0 | 0 | 0 |
| ZM118[pZH8] | 0.11 | 0.08 | 0.5 | 0.5 |
| ZM118[pZH10] | 0.08 | 0.05 | 0.2 | — |
| ZM114[pZH8] | — | — | 0.84 | 0.88 |
| ZM114[pZH10] | 0.10 | — | 0.18 | 0.3 |

Although the foregoing invention has been described in some detail by way of illustration and example for purposes of clarity of understanding, it will be obvious that certain changes and modifications may be practiced within the scope of the appended claims.

What is claimed is:

1. A DNA construct which directs the expression of a thrombin precursor and comprising the following operably linked elements: a transcriptional promoter, a DNA segment encoding a gla-domainless prothrombin and a transcriptional terminator.

2. A DNA construct according to claim 1 wherein the promoter is the mouse metallothionein-1 promoter, the adenovirus major late promoter, the *Saccharomyces cerevisiae* TPI1 promoter or the *Saccharomyces cerevisiae* ADH2-4$^c$ promoter.

3. A DNA construct according to claim 1 wherein the DNA construct further comprises a signal sequence.

4. A DNA construct according to claim 3 wherein the signal sequence is the human tissue plasminogen activator leader sequence, the human α-2 plasmin inhibitor signal sequence, the *Saccharomyces cerevisiae* BAR1 secretory signal sequence or the *Saccharomyces cerevisiae* MFα1 signal sequence.

5. A DNA construct according to claim 1 wherein the DNA segment encodes human gla-domainless prothrombin.

6. A DNA construct according to claim 1 wherein the gla-domainless prothrombin comprises kringle 1, kringle 2, the A chain, an activation site and the serine protease domain of prothrombin; kringle 2, the A chain, an activation site and the serine protease domain of prothrombin; or the A chain, an activation site and the serine protease domain of prothrombin.

7. A DNA construct according to claim 6 wherein the activation site is cleavable by a snake venom activator, thrombin or the *Saccharomyces cerevisiae* KEX2 gene product.

8. A host cell into which has been introduced a DNA construct which directs the expression of a thrombin precursor, said construct comprising the following operably linked element: a transcriptional promoter, a DNA sequence encoding a gla-domainless prothrombin and a transcriptional terminator.

9. A host cell according to claim 8 wherein the DNA construct further comprises a signal sequence.

10. A host cell according to claim 8 wherein the DNA segment encodes human gla-domainless prothrombin.

11. A host cell according to claim 8 wherein the gla-domainless prothrombin comprises kringle 1, kringle 2, the A chain, an activation site and the serine protease domain of prothrombin; kringle 2, the A chain, an activation site and the serine protease domain of prothrombin; or the A chain, an activation site and the serine protease domain of prothrombin.

12. A host cell according to claim 8 wherein said gla-domainless prothrombin contains an activation site cleavable by snake venom activator, thrombin or the *Saccharomyces cerevisiae* KEX2 gene product.

13. A host cell according to claim 8 wherein the host cell is a mammalian or fungal cell.

14. A host cell according to claim 8 wherein the host cell is a yeast cell.

15. A host cell of claim 14 wherein the yeast cell has a mutation in the MNN9 gene, the MNN1 gene, the PMR1 gene or the PEP4 gene.

16. A method for producing thrombin precursor comprising the steps of:
  growing a host cell, into which has been introduced a DNA construct which directs the expression of a thrombin precursor and which DNA construct comprises an operably linked transcriptional promoter, a DNA segment encoding a gla-domainless prothrombin and a transcriptional terminator, under suitable conditions to allow the expression of the thrombin precursor encoded by the DNA segment; and
  isolating the thrombin precursor from the host cell.

17. A method according to claim 16 which further comprises a step of activating the thrombin precursor to thrombin.

18. A method according to claim 16 wherein the DNA construct further comprises a signal sequence.

19. A method according to claim 16 wherein the DNA sequence encodes human gla-domainless prothrombin.

20. A method for producing thrombin comprising the steps of:
  growing a host cell, into which has been introduced a DNA construct which directs the expression of a thrombin precursor and which comprises an operably linked transcriptional promoter, a DNA segment encoding a gla-domainless prothrombin and a transcriptional terminator, under suitable conditions to allow the expression of the thrombin precursor encoded by the DNA segment and its activation to thrombin in the host cell; and
  isolating the activated thrombin from the host cell.

21. A method according to claim 20 wherein the DNA construct further comprises a signal sequence.

22. A method according to claim 21 wherein the DNA sequence encodes human gla-domainless prothrombin.

23. A method according to claim 21 wherein the gla-domainless prothrombin comprises kringle 1, kringle 2, the A chain, an activation site and the serine protease domain of prothrombin; kringle 2, the A chain, an activation site and the serine protease domain of prothrombin; or the A chain, an activation site and the serine protease domain of prothrombin.

24. A method according to claim 23 wherein the activation site is cleavable by a snake venom activator, thrombin or the *Saccharomyces cerevisiae* KEX2 gene product.

25. A method according to claim 16 wherein the host cell is a mammalian or fungal cell.

26. A method according to claim 25 wherein the host cell is a yeast cell.

27. A method of claim 26 wherein the yeast cell has a mutation in the MNN9 gene, the MNN1 gene, the PMR1 gene or the PEP4 gene.

28. A method for producing thrombin comprising the steps of:
  growing a host cell, into which has been introduced a DNA construct which directs the expression of a thrombin precursor and which comprises an operably linked transcriptional promoter, a first DNA segment encoding a signal sequence joined to a second DNA segment encoding a gla-domainless prothrombin and a transcriptional terminator, in a suitable medium and under conditions to allow the expression of the thrombin precursor encoded by said second DNA segment;
  activating the thrombin precursor to thrombin; and
  isolating the thrombin from the medium.

29. A method according to claim 28 wherein the DNA sequence encodes human gla-domainless prothrombin.

30. A method according to claim 29 wherein the gla-domainless prothrombin comprises kringle 1, kringle 2, the A chain, an activation site and the serine protease domain of prothrombin; kringle 2, the A chain, an activation site and the serine protease domain of prothrombin; or the A chain, an activation site and the serine protease domain of prothrombin.

31. A method according to claim 30 wherein the activation site is cleavable by thrombin.

* * * * *